United States Patent
Stone et al.

(10) Patent No.: US 6,694,157 B1
(45) Date of Patent: Feb. 17, 2004

(54) METHOD AND APPARATUS FOR DETERMINATION OF PH PCO₂, HEMOGLOBIN, AND HEMOGLOBIN OXYGEN SATURATION

(75) Inventors: Robert T. Stone, Mountain View, CA (US); Bernhard B. Sterling, Danville, CA (US)

(73) Assignee: Daedalus I , L.L.C., St. Louis, MO (US)

( * ) Notice: Subject to any disclaimer, the term of this patent is extended or adjusted under 35 U.S.C. 154(b) by 0 days.

(21) Appl. No.: 09/247,681

(22) Filed: Feb. 9, 1999

Related U.S. Application Data

(60) Provisional application No. 60/074,254, filed on Feb. 10, 1998.

(51) Int. Cl.⁷ ................................. A61B 5/00
(52) U.S. Cl. .................. 600/310; 600/323; 356/39
(58) Field of Search .................. 600/310, 322, 600/323, 473, 476; 356/39, 40, 41, 300, 317, 320

(56) References Cited

U.S. PATENT DOCUMENTS

| | | |
|---|---|---|
| 4,097,921 A | 6/1978 | Raffaele |
| 4,167,331 A | 9/1979 | Nielsen ...................... 356/39 |
| 4,374,609 A | * 2/1983 | Lange ......................... 359/455 |
| 4,407,290 A | * 10/1983 | Wilber ......................... 600/330 |
| 4,485,820 A | 12/1984 | Flower |
| 4,495,211 A | 1/1985 | Mooiweer ..................... 426/422 |
| 4,579,641 A | 4/1986 | Shimomura et al. ......... 204/403 |
| 4,615,340 A | 10/1986 | Cronenberg et al. |
| 4,704,029 A | 11/1987 | Van Heuvelen .............. 356/39 |
| 4,759,369 A | 7/1988 | Taylor et al. |
| 4,785,814 A | 11/1988 | Kane |
| 4,802,486 A | 2/1989 | Goodman et al. |
| 4,805,623 A | 2/1989 | Jobsis |
| 4,848,901 A | 7/1989 | Hood, Jr. ..................... 356/41 |
| 4,869,254 A | 9/1989 | Stone et al. |
| 4,882,492 A | 11/1989 | Schlager ..................... 250/346 |
| 4,911,167 A | 3/1990 | Corenman et al. |

(List continued on next page.)

FOREIGN PATENT DOCUMENTS

| | | |
|---|---|---|
| WO | WO 90/00572 | 1/1990 |
| WO | WO 95/04266 | 2/1995 |
| WO | WO 98/03847 | 1/1998 |

OTHER PUBLICATIONS

US 4,928,691, 5/1990, Nicolson et al. (withdrawn)

N. Naeraa, E. Strange Petersen and E. Boye; "The Influence of Simultaneous, Independent Changes in pH and Carbon Dioxide Tension on the In Vitro Oxygen Tension–Saturation Relationship of Human Blood", Scandinav.J. Clin. & Lab. Investigation, No. 15; pp. 141–151; 1963.

F. J. W. Roughton and J. W. Severinghaus; "Accurate determination of O2 dissociation curve of human blood above 98.7% saturation with data on O2 solubility in unmodified human blood from 0 to 37 C", Journal of Applied Physiology, vol. 35, No. 6; pp. 861–869; Dec. 1973.

*Primary Examiner*—Eric F. Winakur

(57) ABSTRACT

This invention relates to a method and apparatus for in-vivo, real time measurement of pH, $pCO_2$, base excess, hemoglobin, and hemoglobin oxygen saturation. Specifically, the invention relates to an apparatus placed in-line with an existing invasive patient access line to provide continuous, semi-continuous, or non-continuous monitoring of blood pH, $pCO_2$, base excess, hemoglobin, and hemoglobin oxygen saturation in a manner which is relatively non-invasive. Further, the device and apparatus allows monitoring of the listed parameters in a non-destructive manner such that the blood sample under analysis can be returned to the patient.

38 Claims, 14 Drawing Sheets

U.S. PATENT DOCUMENTS

| | | | |
|---|---|---|---|
| 4,911,230 A | 3/1990 | Mayer et al. ............... 165/48.1 |
| 4,926,867 A | 5/1990 | Kanda et al. |
| 4,928,692 A | 5/1990 | Goodman et al. |
| 4,934,372 A | 6/1990 | Corenman et al. |
| 4,989,606 A * | 2/1991 | Gehrich et al. ............. 600/476 |
| 5,006,105 A | 4/1991 | Sherard ....................... 600/22 |
| 5,009,505 A | 4/1991 | Malvern ..................... 356/352 |
| 5,055,671 A | 10/1991 | Jones .................... 250/227.21 |
| 5,078,136 A | 1/1992 | Stone et al. |
| 5,101,825 A | 4/1992 | Gravenstein et al. |
| 5,104,623 A * | 4/1992 | Miller ........................ 600/323 |
| 5,131,391 A | 7/1992 | Sakai et al. |
| 5,190,039 A | 3/1993 | Takeuchi et al. |
| 5,277,181 A | 1/1994 | Mendelson et al. |
| 5,284,139 A | 2/1994 | Khalil et al. |
| 5,293,875 A | 3/1994 | Stone |
| 5,337,744 A | 8/1994 | Branigan |
| 5,351,686 A | 10/1994 | Steuer et al. |
| 5,355,882 A | 10/1994 | Ukawa et al. |
| 5,357,971 A | 10/1994 | Sheehan et al. |
| 5,362,966 A | 11/1994 | Rosenthal et al. ....... 250/341.1 |
| 5,372,136 A | 12/1994 | Steuer et al. |
| 5,385,143 A * | 1/1995 | Aoyagi ....................... 600/310 |
| 5,402,777 A | 4/1995 | Warring et al. ............. 604/307 |
| 5,404,885 A | 4/1995 | Sheehan et al. |
| 5,412,510 A | 5/1995 | Iizuka et al. ................ 359/820 |
| 5,414,648 A | 5/1995 | Morgan et al. ............. 364/563 |
| 5,421,329 A | 6/1995 | Casciani et al. |
| 5,423,327 A | 6/1995 | Clauson et al. |
| 5,427,093 A | 6/1995 | Ogawa et al. |
| 5,428,323 A | 6/1995 | Geissler et al. ............. 333/135 |
| 5,429,594 A | 7/1995 | Castle ........................... 604/4 |
| 5,431,159 A | 7/1995 | Baker et al. |
| 5,433,197 A | 7/1995 | Stark |
| 5,445,157 A | 8/1995 | Adachi et al. |
| 5,448,992 A | 9/1995 | Kupershmidt |
| 5,452,717 A | 9/1995 | Branigan et al. |
| 5,453,248 A | 9/1995 | Olstein .................... 422/82.07 |
| 5,462,052 A | 10/1995 | Gehrich et al. |
| 5,469,845 A | 11/1995 | DeLonzor et al. |
| 5,480,723 A | 1/1996 | Klainer et al. ............. 428/441 |
| 5,492,118 A | 2/1996 | Gratton et al. |
| 5,497,771 A | 3/1996 | Rosenheimer |
| 5,499,627 A | 3/1996 | Steuer et al. |
| 5,503,148 A | 4/1996 | Pologe et al. |
| 5,517,987 A | 5/1996 | Tsuchiya .................... 600/328 |
| 5,525,518 A | 6/1996 | Lundsgaard et al. .......... 436/68 |
| 5,526,808 A | 6/1996 | Kaminsky |
| 5,536,783 A | 7/1996 | Olstein et al. ............. 525/129 |
| 5,553,615 A | 9/1996 | Carim et al. |
| 5,604,584 A | 2/1997 | Iwasaki ...................... 356/218 |
| 5,607,644 A | 3/1997 | Olstein et al. ........... 422/82.07 |
| 5,632,958 A | 5/1997 | Kane et al. ............... 422/82.07 |
| 5,642,734 A | 7/1997 | Ruben et al. |
| 5,656,241 A | 8/1997 | Seifert et al. ............. 422/82.06 |
| 5,672,515 A | 9/1997 | Furlong ..................... 436/133 |
| 5,681,532 A | 10/1997 | Kane et al. ............... 422/82.06 |
| 5,817,007 A | 10/1998 | Fodgaard et al. ........... 699/322 |
| 5,978,691 A | 11/1999 | Mills .......................... 600/334 |
| 6,010,747 A * | 1/2000 | Beeson et al. .............. 427/162 |

* cited by examiner

METHOD AND APPARATUS FOR DETERMINATION OF PH PCO$_2$, HEMOGLOBIN, AND HEMOGLOBIN OXYGEN SATURATION

This application claims the benefit of provisional application 60/074,254 filed Feb. 10, 1998.

FIELD OF THE INVENTION

This invention relates to a method and apparatus for in-vivo, real time measurement of pH, pCO$_2$, base excess, hemoglobin, and hemoglobin oxygen saturation. More particularly, the invention relates to an apparatus placed in-line with an existing invasive patient access line to provide continuous, semi-continuous, or non-continuous monitoring of blood pH, pCO$_2$, base excess, hemoglobin, and hemoglobin oxygen saturation in a manner which is relatively non-invasive. Further, the device and apparatus allows monitoring of the listed parameters in a non-destructive manner such that the blood sample under analysis can be returned to the patient.

BACKGROUND OF THE INVENTION

Although body fluid analyzers are known in the art, presently available sensors use electrochemical sensors, also known as electrodes to measure blood parameters such as pH and pCO$_2$. See U.S. Pat. Nos. 3,874,850; 4,097,921; 4,579,641; 4,615,340. Such electrode measurement techniques often require a great deal of costly equipment and frequent maintenance. Typically, an elaborate 2-point calibration is required. Acceptable accuracy with reusable electrochemical systems is obtained only with an additional step of cleaning the electrodes with a washing solution after each use. The alternative approach to electrochemical sensors utilized in the method and apparatus described herein is based upon the hydrogel dye film sensing elements described in international publication number WO 90/00572.

The determination of blood pH, pCO$_2$, hemoglobin, and hemoglobin oxygen saturation include in-vivo techniques by which a blood sample is withdrawn from a patient and sent to a laboratory for analysis. This technique has several drawbacks. The blood sampling and transfer to a laboratory requires addition of anti-coagulants or other preservative agents rendering the sample unsuitable for return to the patient. The blood sample tested reflects a single measurement and does not provide any indication of stability or fluctuation over time. Laboratory in-vivo methods do not permit continuous monitoring of blood pH, pCO$_2$, hemoglobin, and hemoglobin oxygen saturation. Means for obtaining a blood sample for study involve invasive techniques and thus pose risks of infection or introduction of emboli to the bloodstream. Frequently, repeated measurements deplete blood volume, particularly of infants and small children, and involve repeated risk exposure. The time elapse between sample withdrawal and analysis delays complete diagnosis and determination of course of treatment for a patient who may be critically ill.

Oximeters have been utilized for in-vivo determinations of blood hemoglobin oxygen saturation, but have not been used to provide information on hemoglobin concentration. Such methods employ "naturally occurring cuvettes", for example, the earlobe or the finger. Results obtained with these oximeters are often adversely affected by interference from venous blood, tissue, bone, ambient light, or patient motion.

Limitations encountered in some in-vivo oximeters have led to the development of intravascular oximeters. Such devices employ some indwelling components in a vessel and obtain saturation by reflection spectrophotometry.

Spectrophotometric techniques used to determine blood hemoglobin oxygen saturation may be subject to measurement error caused by the presence of dyshemoglobins in the blood sample. Dyshemoglobins, such as methemoglobin and carboxyhemoglobin, cannot transport oxygen but possess spectral absorbance which may interfere with the absorbance of oxyhemoglobin, depending upon the wavelength of the incident light used.

Spectrophotometric measurements of blood hemoglobin oxygen saturation and hemoglobin concentration of non-hemolyzed whole blood are difficult and require sophisticated mathematical models, and cannot achieve clinical accuracy.

SUMMARY OF THE INVENTION

It is an object of the present invention to provide an in-vivo, real time measurement of blood pH, pCO$_2$, hemoglobin oxygen saturation by means of an apparatus which is placed in-line with existing invasive patient access lines.

It is a further object of the present invention to provide an apparatus which does not limit access line function, and yet, may be used to provide continuous or non-continuous monitoring of blood pH, pCO$_2$, hemoglobin and hemoglobin oxygen saturation.

It is a further object of the present invention to provide a means of rapidly determining the measurement of blood pH, pCO2, and hemoglobin oxygen saturation in a manner which utilizes a minimal blood volume in such a manner that the blood is not tested destructively, and may be returned to the patient.

And, it is a still yet a further object of the present invention that the sensors and blood chambers utilized in the measuring process be comprised of a sterile disposable cuvette which eliminates the need for cleaning and/or sterilizing of the instrument, and which eliminates the need for frequent calibration of the device.

These and other objects of the invention are realized in a preferred embodiment of the present invention.

The apparatus is comprised of: 1) a disposable cuvette containing blood chambers and sensors for measurement of pH, pCO$_2$, hemoglobin, and hemoglobin oxygen saturation, 2) a readout head containing the means of detecting the signals from the sensors, 3) electronic circuitry for processing and conditioning the electronic signals from the readout head, 4) computer circuitry to analyze the signals and compute the resultant pH, pCO$_2$, hemoglobin, and hemoglobin oxygen saturation, 5) computer software to use in processing the signals, and 6) display means to provide the results to the user.

The present invention also provides a method of determination of hemoglobin and hemoglobin oxygen saturation by means of combining a multi-chambered sampling cuvette with photo-sensors for pH and pCO$_2$, optically diffusing walls and a separate chamber for diffuse transmittance determination of hemoglobin and hemoglobin oxygen saturation, and a subminiature spectrophotometer measurement system with a dual channel transmission/reflectance system for pH and pCO$_2$ measurement, and a further diffuse transmission system for hemoglobin and hemoglobin oxygen saturation measurement. This method and apparatus allows continuous monitoring of the most common blood analyses performed on critically ill patients.

The method provides the measurements without requiring handling of body fluid samples. Further, the method provides the measurements in a rapid fashion without the otherwise wait for laboratory procedures to be accomplished. Further, the method provides the measurements without destruction or contamination of the sample, allowing the sample to be returned to the patient. Further, the method allows repeat measurements with the same sensor without requiring cleaning of the sensor between measurements.

DETAILED DESCRIPTION OF THE INVENTION

Figure 1:
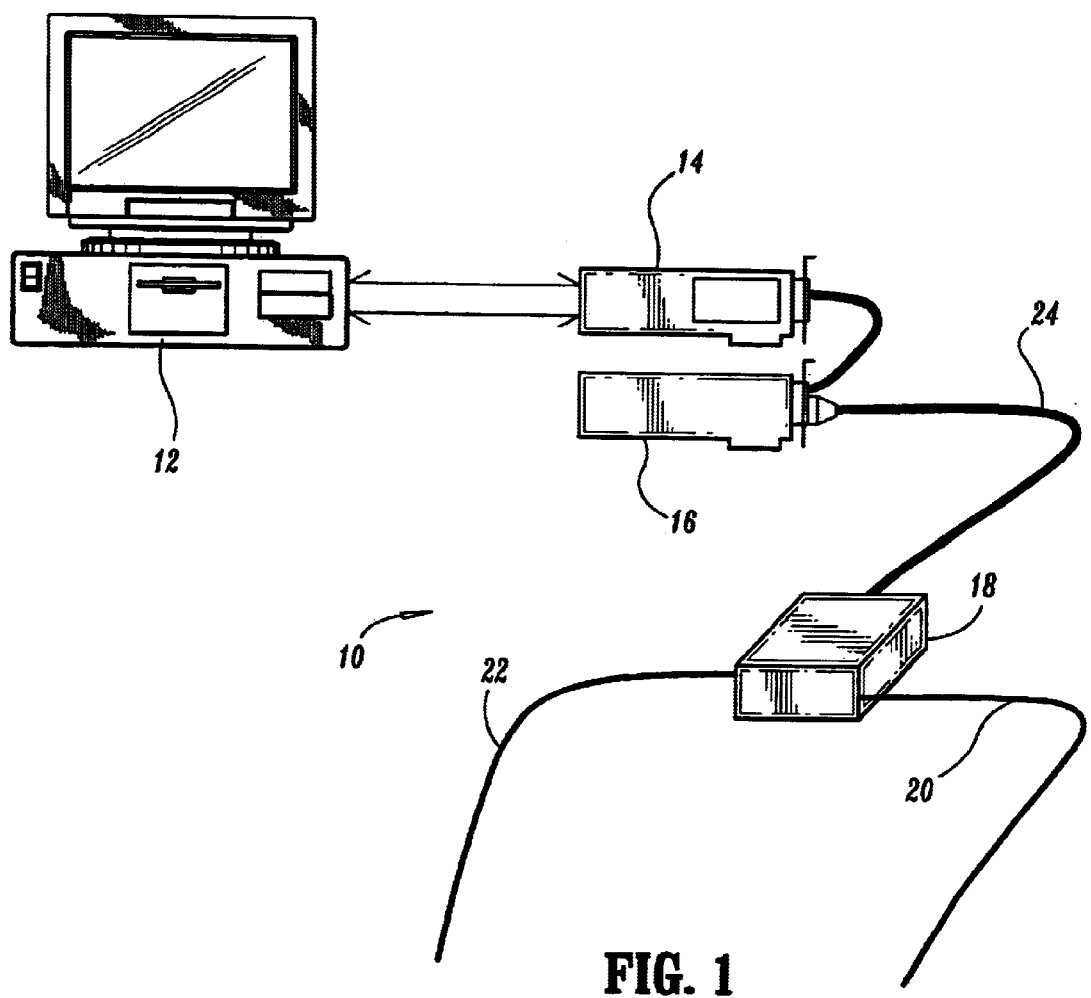
FIG. 1 is a functional block diagram of the apparatus components.

Referring to FIG. 1, the measuring device 10 of the present invention is comprised of a system of several components, specifically: a general purpose computing device 12 (i.e., such as an IBM PC compatible computer) for control and display, a first interface card 14 which contains the necessary electronic control and signal conditioning circuitry, and a second interface card 16, a subminiature spectrophotometer 18 which provides specific wavelength visible and infra-red light sources and light intensity detection sensors, a cuvette suitable for introduction of blood or other body fluid for analysis, containing the pH and pCO$_2$ sensing dye layers, and an appropriate connective tubing 20 and 22 to invasive patient monitoring lines for introduction of body fluid sample and for return of the samples to the patient, respectively.

Specifically, the general purpose IBM PC compatible computer 12 displays the measured values, provides user control, and stores the operating instructions or programs for the measuring device. The first interface card 14 is an Analog to Digital interface card, preferably a Data Translation type DT2801, and the second interface card 16 is a specialized spectrophotometer interface card as hereinafter described. The spectrophotometer interface card 16 is connected by electrical cable 24 to the subminiature spectrophotometer 18 which houses the measurement cuvette, both discussed hereinbelow. The measurement cuvette is connected to a source of blood for analysis (not shown) which may be indwelling invasive patient lines or may be a syringe or other container of blood for measurement.

Figure 2:
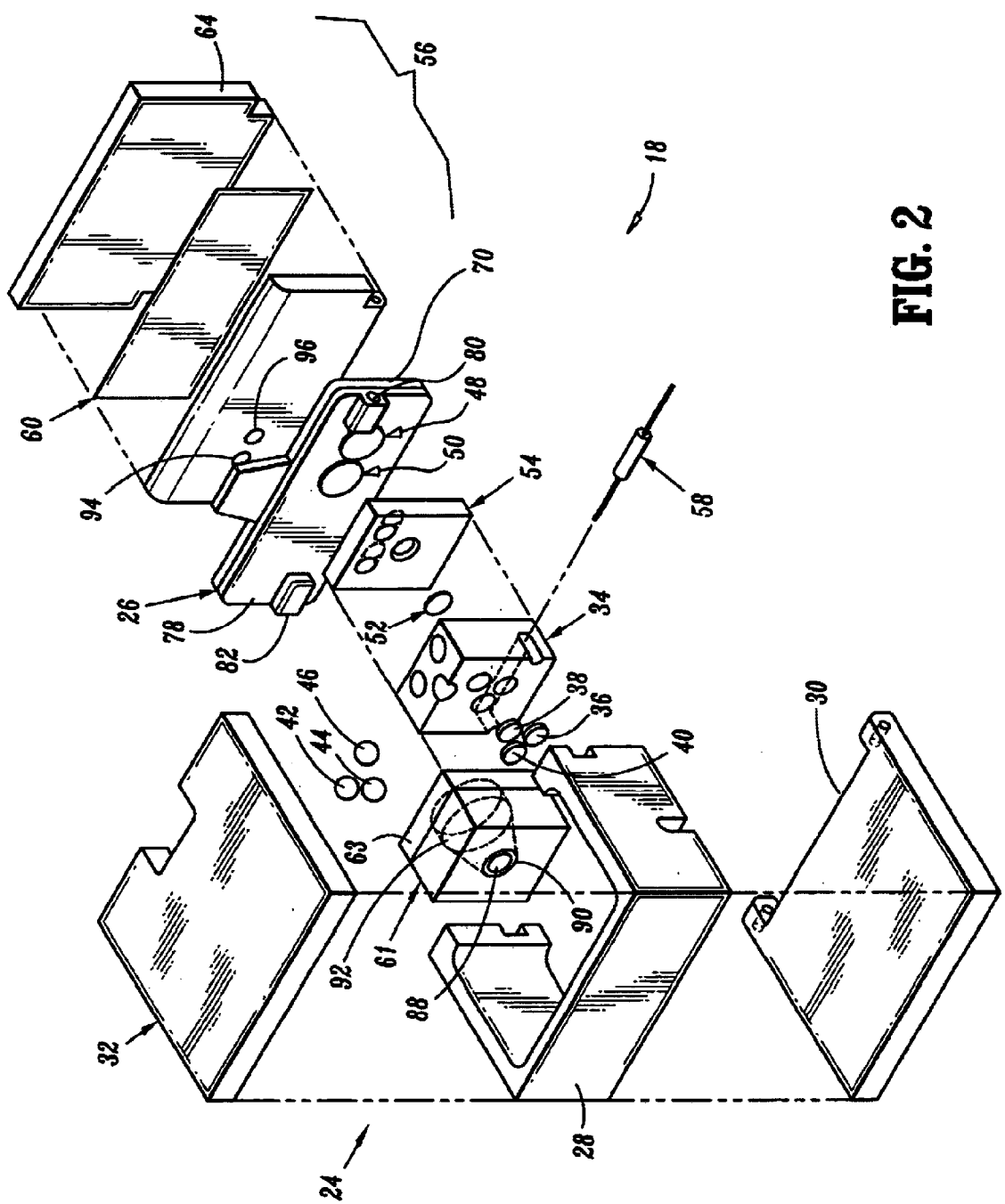
FIG. 2 is exploded assembly drawing of the spectrophotometer of the present invention.
Figure 3:
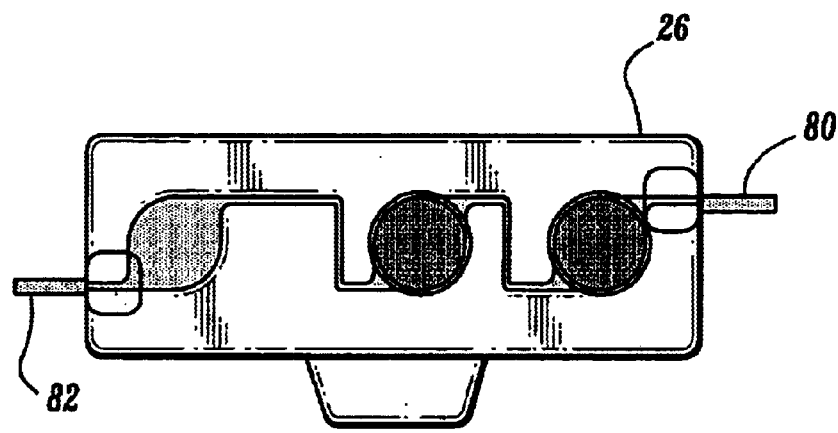
FIG. 3 is a cross sectional view of the cuvette of the present invention taken along line 3—3 of FIG. 2.
Figure 4:
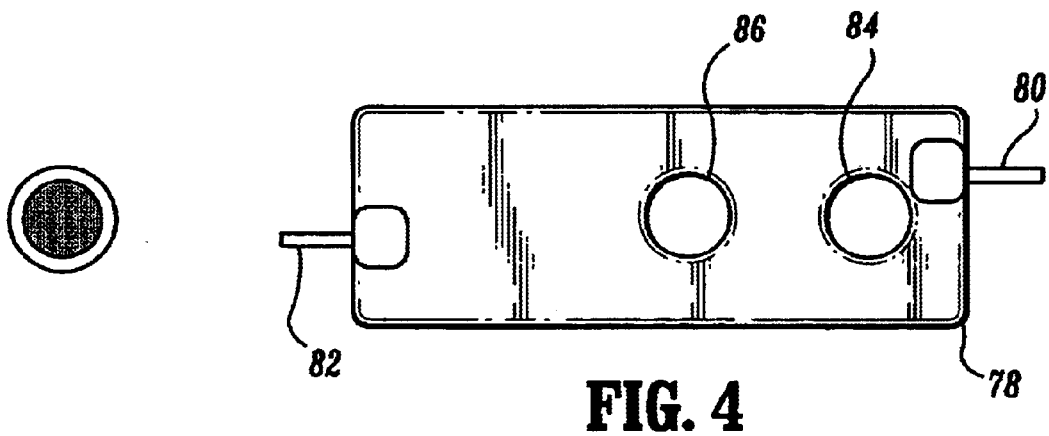
FIG. 4 is a cross sectional view of the sensor chamber of the cuvette of the present invention.

Referring now to FIGS. 2 through 4, the subminiature spectrophotometer 18 of the measuring device 10 of the present invention and operation thereof for rapid continuous measurement of blood pH and pCO$_2$, hemoglobin, and hemoglobin oxygen saturation is shown.

Referring specifically to FIG. 2, the spectrophotometer 18 is shown in greater detail with an exploded view of the various components of the spectrophotometer 18. The spectrophotometer includes the readout head 24 and cuvette 26. The readout head 24 includes a readout head body 28 having base plate 30 and top cover 32. Inside of readout head 24 is a first machined block housing 34 which houses three light sources 36, 38 and 40, preferably at 550, 630, and 910 nanometers, respectively, and three photodiodes 42, 44, 46, one each for the determination of the pH, pCO$_2$, and reference light intensity measurements, respectively. The cuvette 26 is a molded assembly for containing the blood sample to be measured, and is provided with a pH sensor 48, and a pCO$_2$ sensor 50. Sensors 48 and 50 are assemblies of pH sensitive hydrogel, reflective layers, opaque layers, and appropriate blood contact layers further described in FIGS. 8 and 9. Such sensors are more fully discussed in WO 90/00572, which is hereby incorporated by reference. Adjacent housing 34 is an optical diffuser 52 which provides for uniform distribution of light to both the pH sensor 48 and pCO$_2$ sensor 50 within the cuvette 26. A first optical coupling block 54 is positioned between housing 34 and cuvette 26 to act as a spacer and provide for the proper distribution of light from the light sources through the diffuser 52 to the pH and pCO$_2$ sensors 48 and 50, respectively, and then back to the photodiodes 42, 44, and 46 while preventing stray light from reaching the photodiodes. The cuvette 26, which is more fully discussed below in relation to FIGS. 3–6, is provided with an arterial blood input line 20 to bring the blood sample into one side of the cuvette 26 and a blood return line 22 for returning the blood to the patient. The readout head 24 is constructed so that the cuvette 26 can be placed within the measuring device through a hinged front access door 56. It is important to maintain the blood sample at a constant temperature, preferably 37 degrees centigrade, therefore the measuring device is provided with several heaters. A first resistive heating element 58 is provided within the light source block housing 34. A second flat ribbon heating element 60 is provided between a readout head door plate 62 and a door cover 64. The door plate 62 provides thermal coupling to the cuvette 26 for maintaining the blood sample at the proper temperature for measurement of the pH and pCO$_2$.

Further referring to FIG. 2, a second machined block housing 61 is shown adjacent first block housing 34. The block housing 61 houses two light sources 88 and 90 at the hemoglobin/hemoglobin oxygen measurement wavelengths of 660 nanometers and 920 nanometers. A second optical coupling block 63 is positioned between housing 61 and cuvette 26 to act as a spacer and provide for the proper distribution of light from the light sources 88 and 90, through a diffuser 92, preferably made out of white Teflon® which is positioned within the coupling block 63. The light from LEDs 88 and 90 is diffused by diffuser 92, and transmitted through the cuvette body to the third blood sample chamber 76 to a transmission intensity sensor 94 which is positioned in the readout head door plate 62. A portion of the light from LEDs 88 and 90 is also transmitted only through the cuvette body and not through the third blood sample chamber 76 to a reference intensity sensor 96 also positioned in the readout head door plate 62. Light sensors 94 and 96 preferably consist of photodiodes.

The diffuser 92 may alternatively be made out of an optically clear plastic material in which approximately 1% titanium oxide crystals have been uniformly mixed. In such materials as have been described herein for use for the diffuser 92 and the cuvette 26 (as described below) it is important that the diffusion of light be relatively indistinguishable from that characteristic of the whole blood (i.e., the light is so dispersed by the diffuser and cuvette that further diffusion by the whole blood is not significant to the transmitted light intensity).

Figure 5:
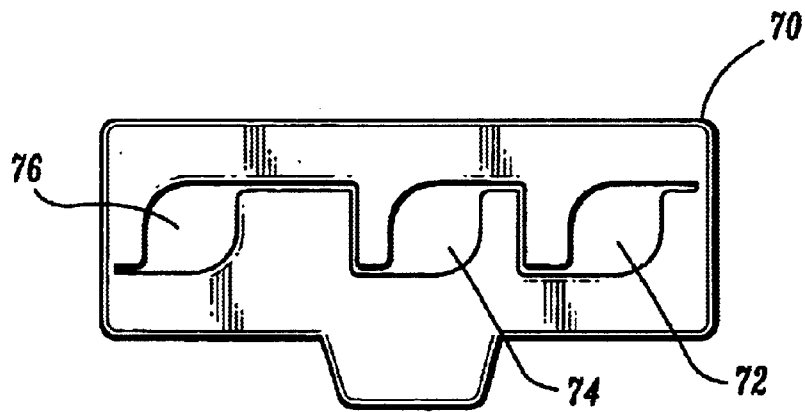
FIG. 5 is a cross sectional view of the sample chambers of the cuvette of the present invention.

Referring now to FIGS. 3–5, the cuvette 26 which can be made out of optically diffuse plastic, preferably a thermal injection molded plastic such as polycarbonate in which titanium dioxide particles are dispersed is assembled from two pieces. Referring to FIG. 5, the front half 70 of the cuvette 26 forms the first and second sample chambers 72 and 74, respectively for determination of pH and $pCO_2$ and a third sample chamber 76 for analysis of hemoglobin and hemoglobin oxygen saturation. Referring to FIG. 4, the back half of the chamber 78 contains blood inlet port 80 and outlet port 82 for connection to blood input line 20 and blood return line 22, respectively, and holes 84 and 86 for sealingly attaching pH and $pCO_2$ sensors 48 and 50, respectively. In reference to the drawings the back and front of the cuvette relate to directions facing either towards the back of the body 28 or towards the front hinged access door 56. Preferably, the two halves 70 and 78 of the cuvette are assembled by adhesive means such as ultrasonic welding or sonic bonding. FIGS. 2 and 3 show the two halves of the cuvette together to form the assembled cuvette 26.

The assembled cuvette 26 is comprised of materials that are biologically inert, and is preferably assembled and packaged in such a manner as to be sterile prior to removal from its container for application.

Figure 6:
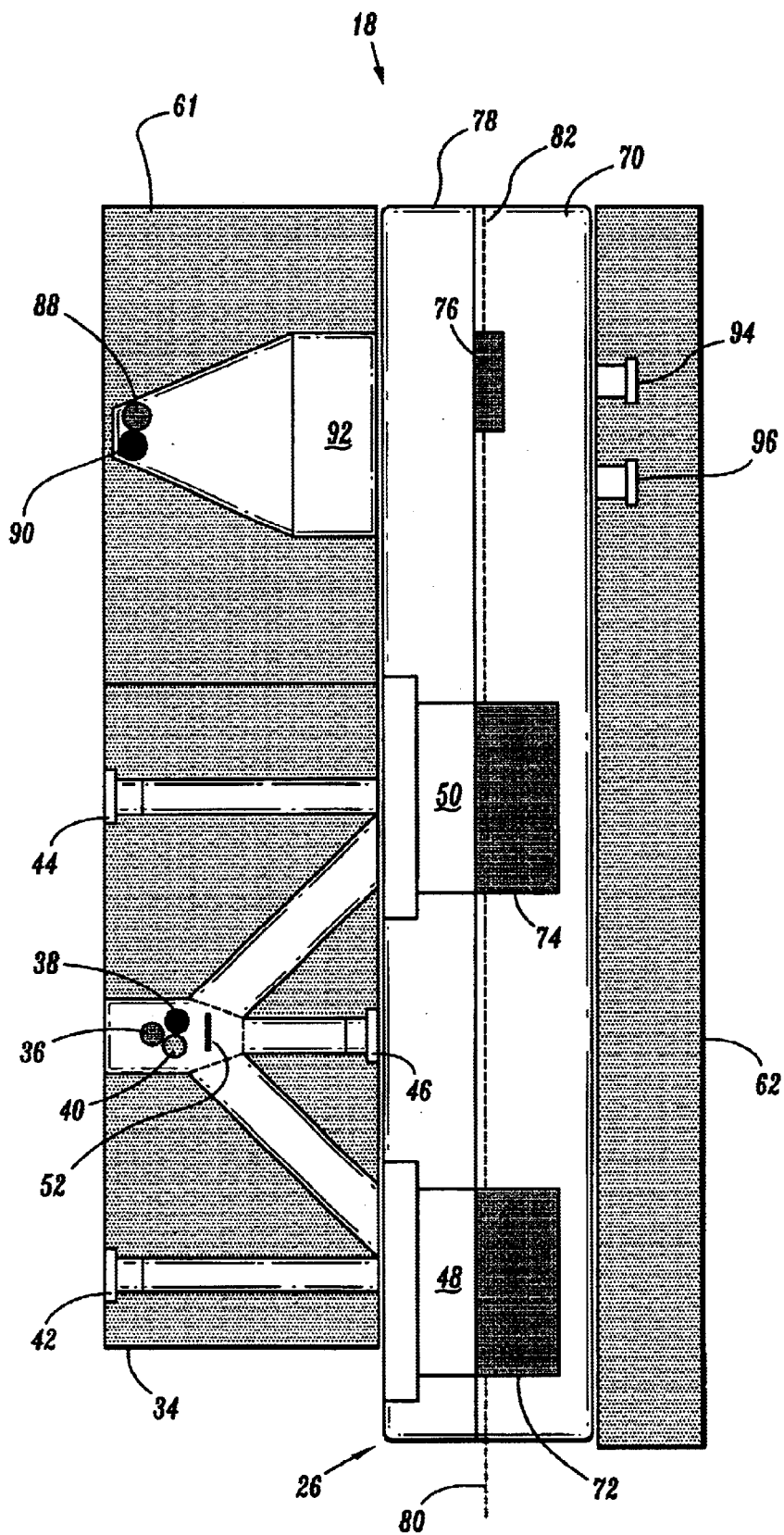
FIG. 6 is a functional detail drawing of the readout head and cuvette of the present invention.

Referring to FIG. 6, the subminiature spectrophotometer 18, including both the readout head 24 and cuvette 26 is shown diagrammatically. Blood is introduced into the cuvette via inlet port 80, filling the measurement chambers 72 and 74 beneath the pH sensor 84 and the $pCO_2$ sensor 86 and passing into the third blood sample chamber 76, and leaving the cuvette via exit port 82. The cuvette and the enclosed blood are maintained at the appropriate measurement temperature, preferably 37 Celsius, by the first resistive heater 58 within the block housing 34 and the second flat ribbon heater 60 integral to the access door 56. Light at the pH/$pCO_2$ measurement wavelengths, preferably 550 nanometers, 630 nanometers, and 920 nanometers is supplied in the preferred embodiment by light sources or LEDs 36, 38, and 40. These frequencies are particularly useful in determining the pH of AZO dyes described in PCT publication number WO 90/00572, incorporated herein by reference. Other appropriate wavelengths could be used. The initial intensity of the pH LEDs is measured by reference photodiode 46. The light absorption of the pH sensitive dye layers is measured by the intensity of reflected light as measured by photodiodes 42 and 44. Light at the hemoglobin/hemoglobin oxygen measurement wavelengths, preferably LEDs with mean emission wavelengths of 660 nanometers and 920 nanometers is supplied by LEDs 88 and 90. The light is diffused by diffuser 92 and transmitted through cuvette body to the third blood sample chamber 76, and to the transmission intensity sensor 94. As discussed above, a portion of the light is also transmitted through just the cuvette body to the reference intensity sensor 96.

Referring to blood chamber 76, it is important that the thickness of the blood chamber 76 be controlled so that the thickness is in the range of 0.020 inches to 0.040 inches, and preferably, that the thickness of the blood chamber be 0.030 inches plus or minus 0.0003 inches. The thickness of blood chamber 76 is important so that sufficient attenuation of light is obtained for accurate determination of hemoglobin and de-oxyhemoglobin concentrations without significantly affecting the dispersion angle of the light transmitted through the blood sample.

Figures 7, 7A:
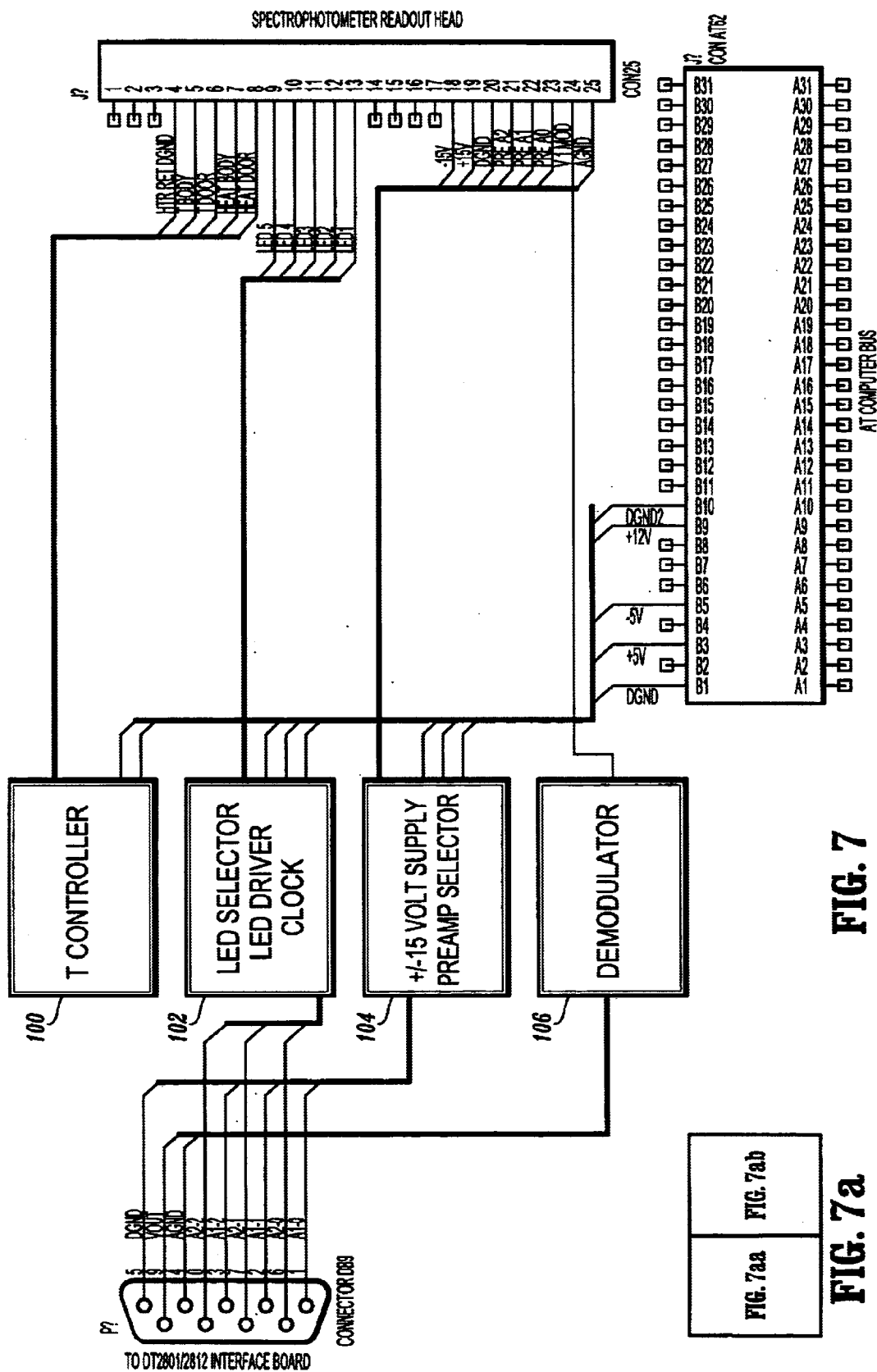
FIG. 7 is a block diagram of the spectrophotometer interface circuit and subcircuits required for use by the measuring apparatus.
FIG. 7a is a detailed circuit schematic of the preferred embodiment of the electric circuity within the readout head of FIG. 7.
Figure 7A:
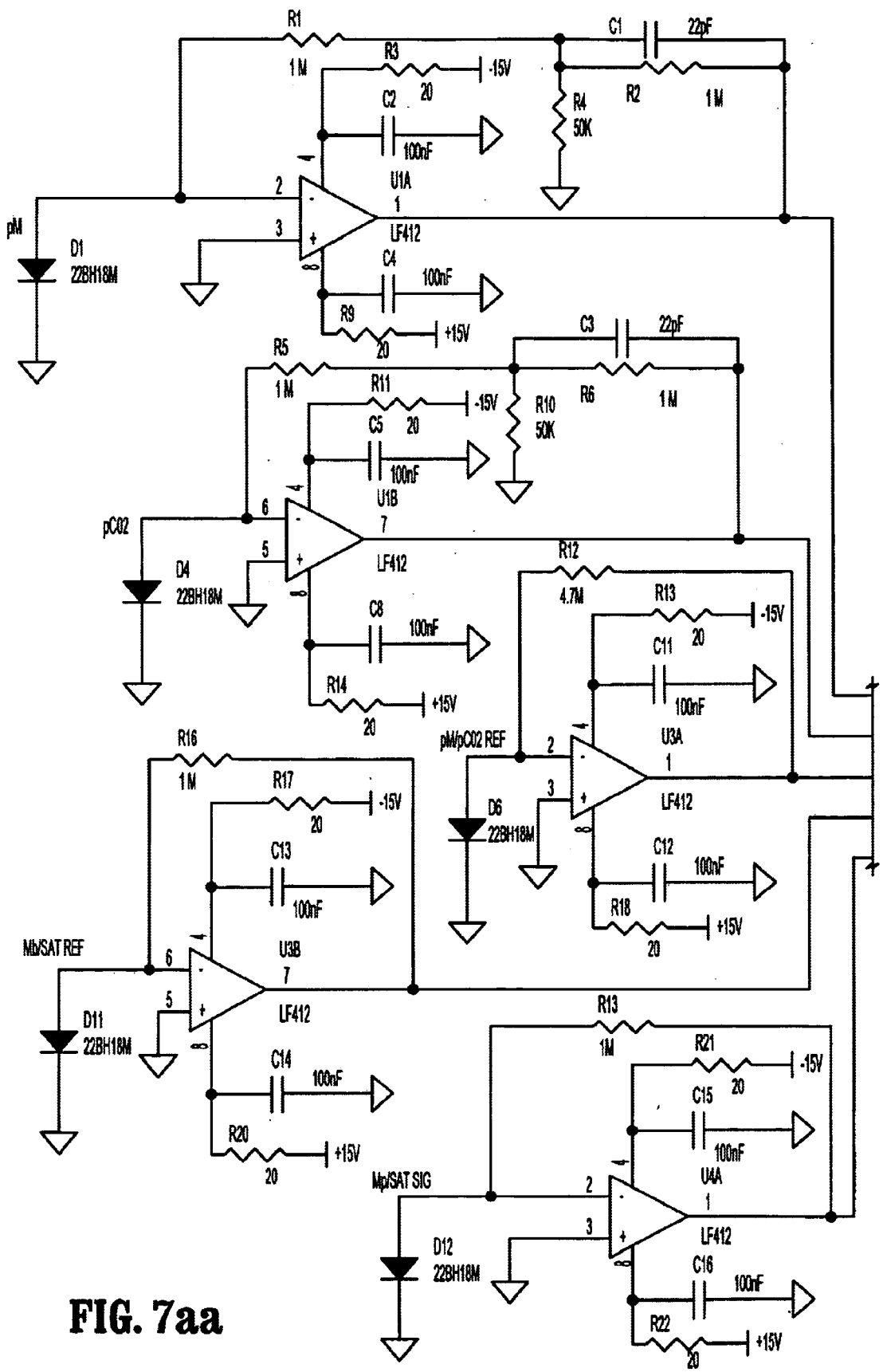
Figure 7A:
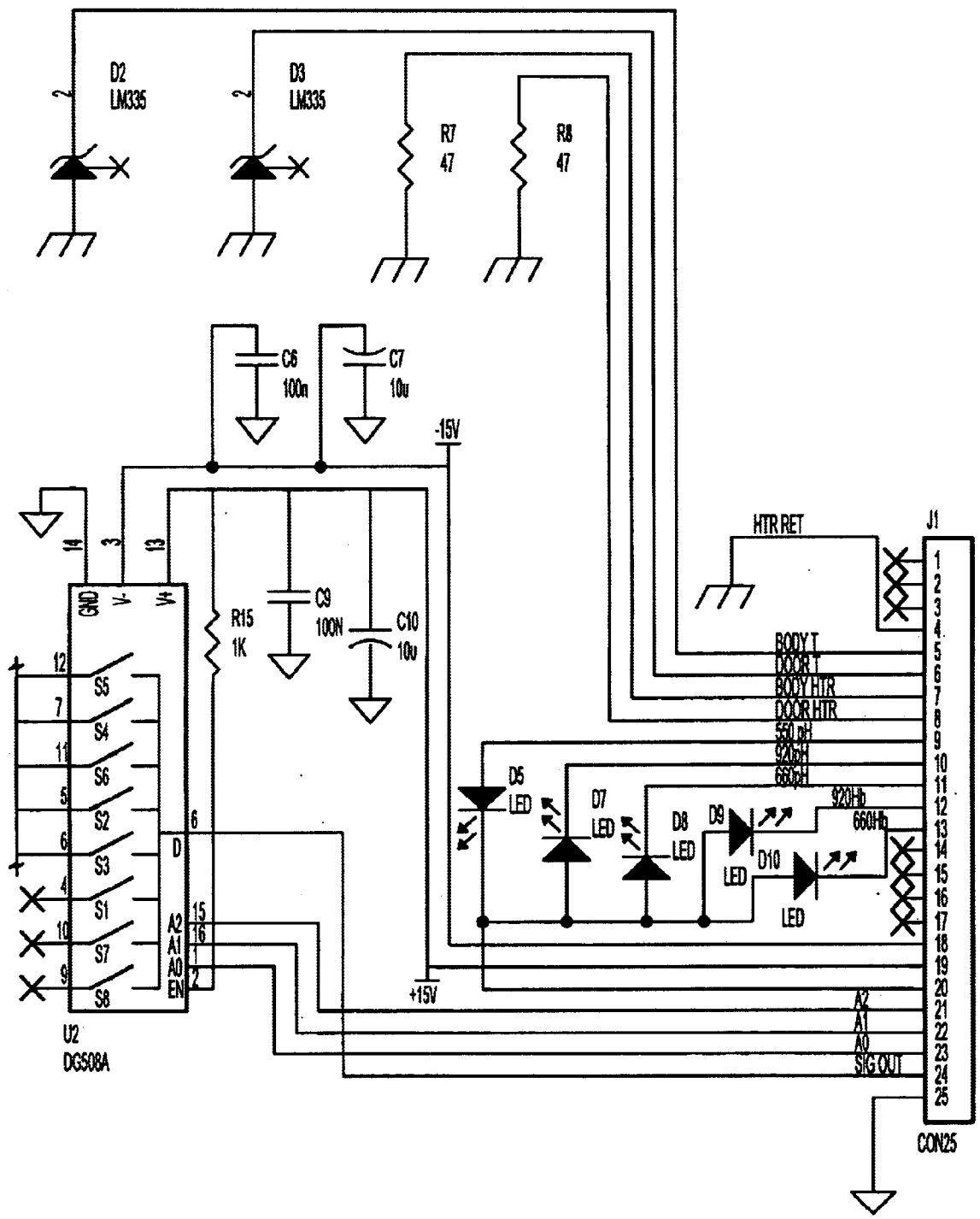

FIG. 7 shows a block diagram of the spectrophotometer interface circuit and FIGS. 7a through 7g show details of the subcircuits required for the measurement process. These subcircuits shown in block diagram form in FIG. 7 consist of two temperature regulator circuits 100 which maintain the readout head body 34 and door 56 at preferably 37 Celsius; LED driver, selector, and clock circuit 102 which selectively illuminates the LED's as instructed by microprocessor control; power supply and preamplifier circuit 104 for amplification of the electrical signals from each of the photodiodes; and demodulator subcircuit 106 which detects and filters the signals in preparation for quantitation by the analog to digital interface board.

Referring to FIG. 7a, LEDs D5, D7, D8, D9 and D10 are sequentially driven on and off by electronic circuitry contained in the spectrophotometer readout head 24 at a frequency chosen to be removed from that of ordinary room lights or their harmonic frequencies. By stroking the LEDs sequentially, the resulting signals at photodiodes D1, D4, D6, D11, and D12 may be separated into multiple signals. Six signals each representing the transmission of light through the pH or $pCO_2$ dye layer at the different wavelengths, and three separate signals representing the initial or reference intensity of the light sources are representative of the pH and $pCO_2$ measurements. Four additional signals are representative of the transmitted and reference intensity for the hemoglobin and hemoglobin oxygen saturation measurement.

To eliminate any undesired effect of background light on the photodiode, two phases of LED stroking and light detection are established by the electronic circuitry. The selected LED is pulsed on, and its transmitted light together with any stray background light is detected by the photodiode, only during phase 1. During phase 2 the photodiode detects only background light. By alternatively detecting and then positively amplifying both LED light plus background light, and then detecting and negatively amplifying only background light, on average the background light photo currents will be canceled from the resulting amplified signal.

FIG. 7a shows a schematic diagram of a preferred embodiment of the electronic circuitry in the readout head 24 capable of detecting the light transmissions through the pH and pCO$_2$ sensitive gel layers. The three LEDS D5, D7, and D8 and each of the photodiodes, D1, D4, and D6 are mounted at a 45 degree angle to each other, and at 45 degrees to the horizontal plane of the pH sensing gel layer in contact with the specimen fluid. Voltages 550 pH, 920 pH, and 660 pH drive the LEDs D5, D7, and D8 respectively, during measurement phases for each of the three colors simultaneously for the pH and pCO$_2$ sensors. The output of photodiodes D1, D4, and D6 are shown in FIG. 7a driving high gain preamplifier stages U1A, U1B and USA which convert photodiode currents to voltages.

FIG. 7a also shows a schematic diagram of a preferred embodiment of the electronic circuitry in the readout head capable of detecting the light transmissions through the blood for measurement of hemoglobin and hemoglobin oxygen saturation. Voltages 920 Hb and 660 Hb drive the LEDs D9 and D10 respectively, during measurement phases for transmission and reference intensity sensors, D12 and D11. The output of photodiodes D11 and D12 are shown in FIG. 7A driving high gain preamplifier stages U3B and U4A which convert photodiode currents to voltages.

The voltages from each of the preamplifier stages are fed to voltage multiplexer U2. Each of the preamplifier voltages is electronically selected by the microprocessor for amplification and detection. Selection signals, A0, A1, and A2 are provided by the microprocessor for selecting each preamplifier for measurement.

Figure 7B:
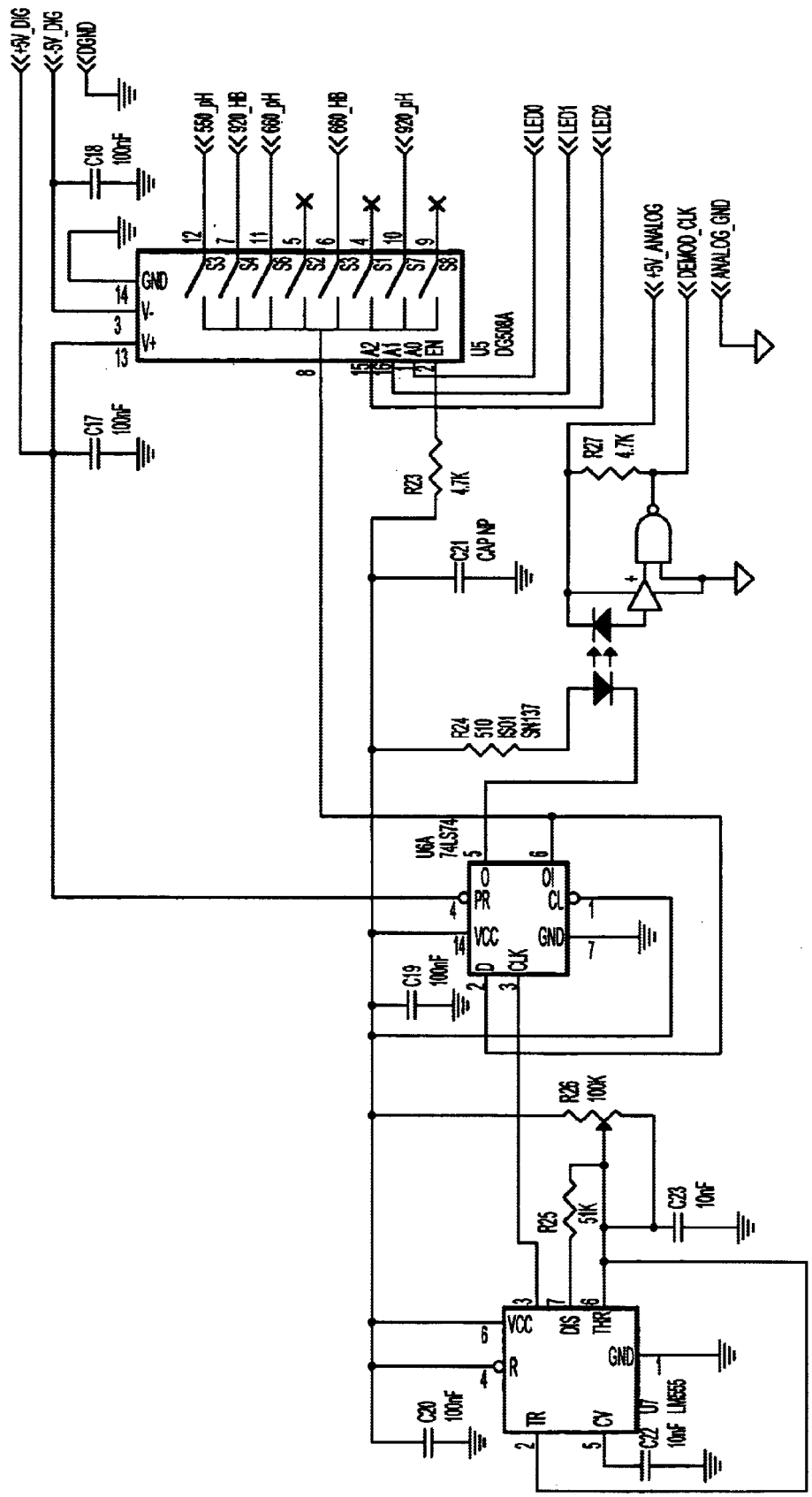
FIG. 7b and 7c are detailed circuit schematics of the preferred embodiment of the electric circuity of the LED selector and driver of FIG. 7.
Figure 7C:
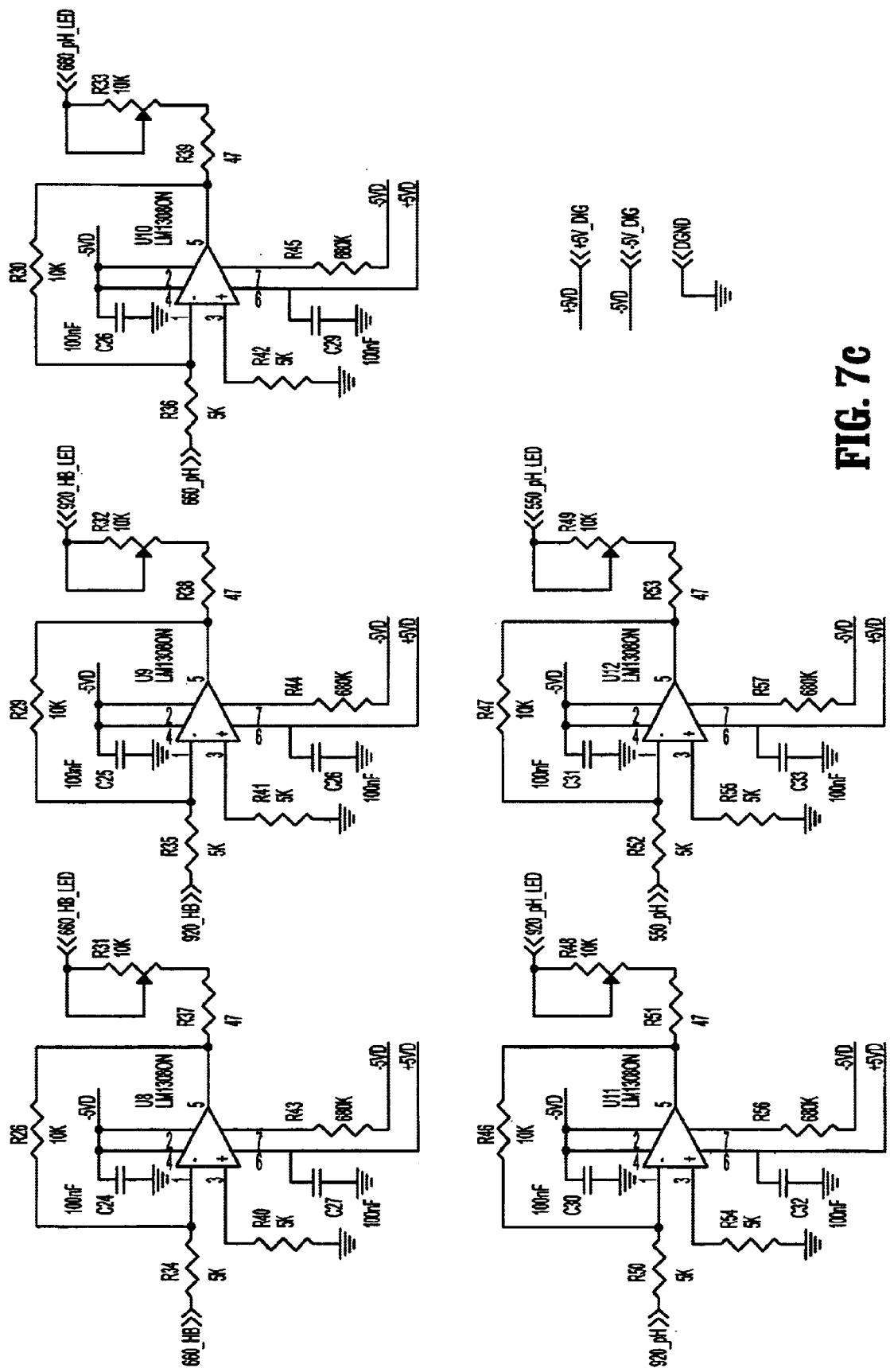
Figure 7D:
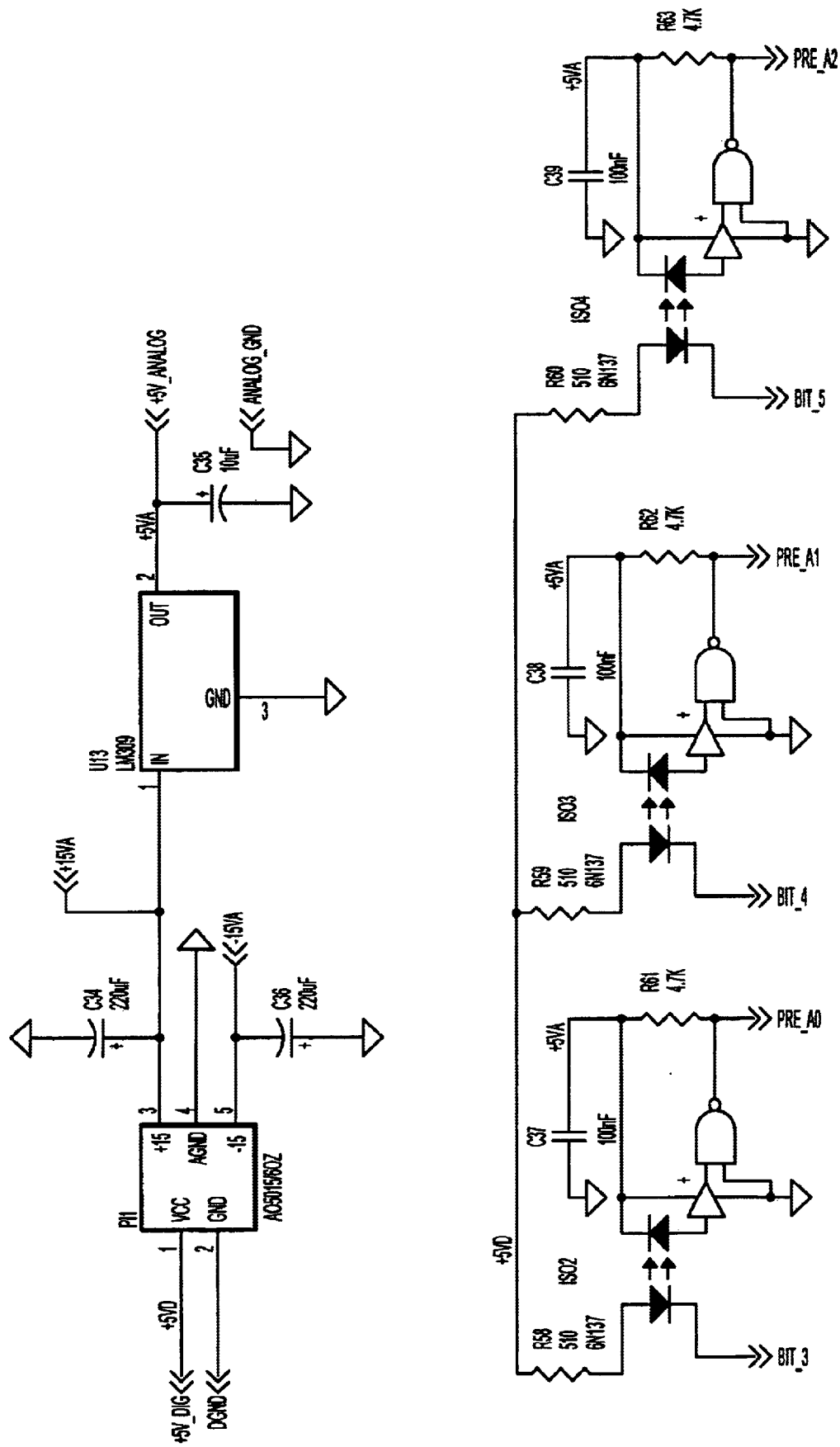
FIG. 7d is a detailed circuit schematic of the preferred embodiment of the electric circuitry of the power supply and interference board of FIG. 7.
Figure 7E:
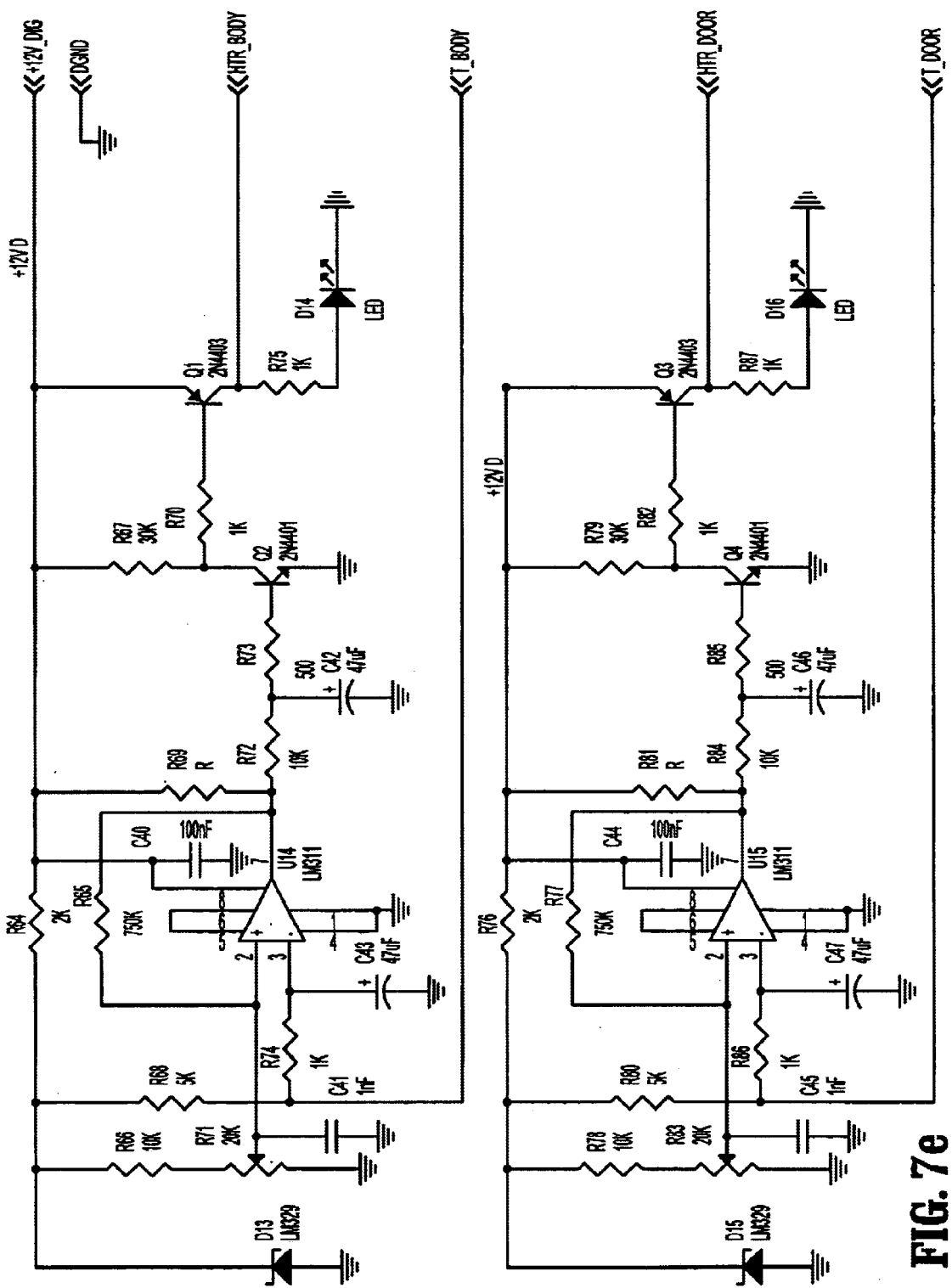
FIG. 7e is a detailed circuit schematic of the preferred embodiment of the electric circuitry of the temperature controller of FIG. 7.
Figure 7F:
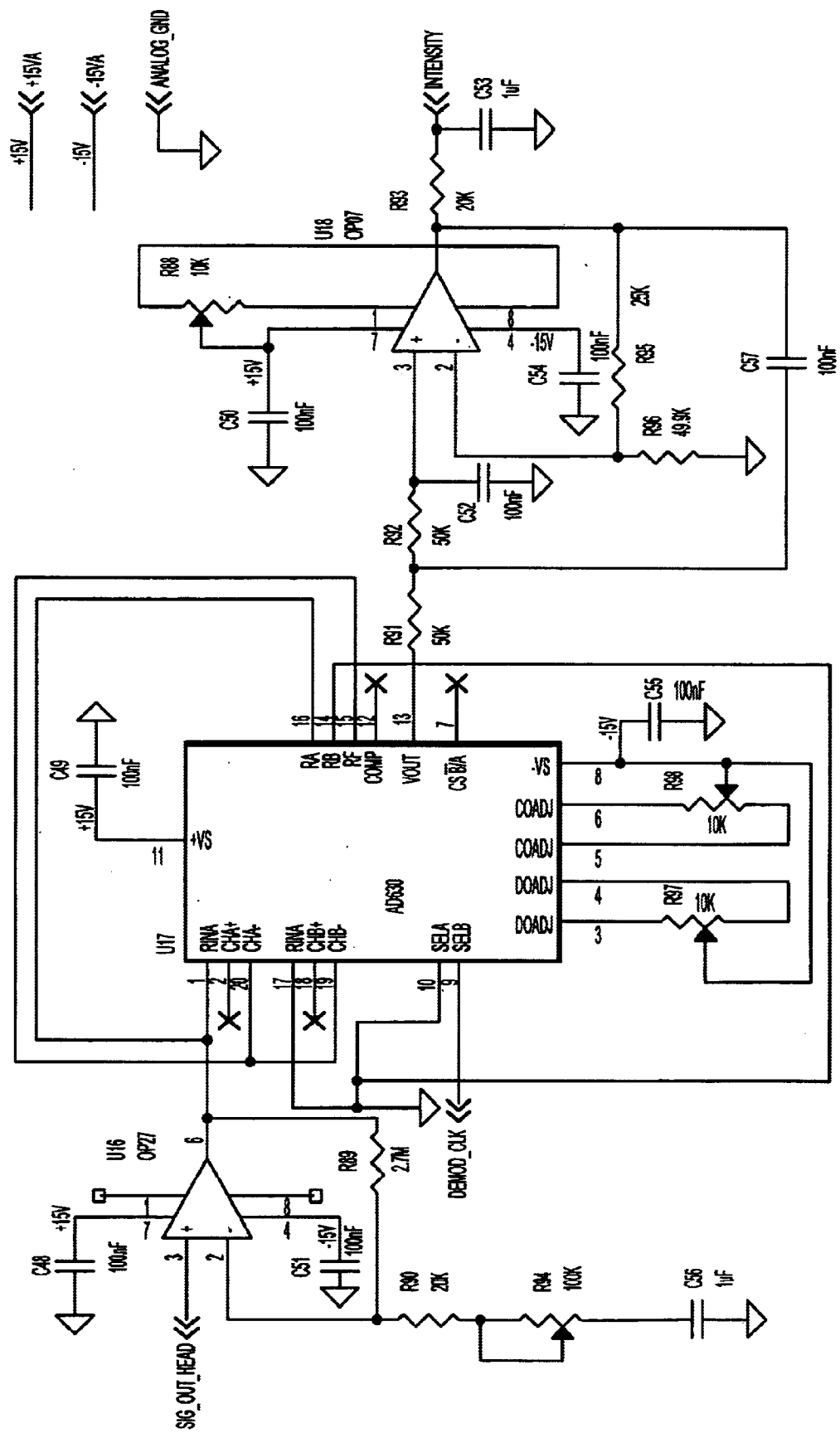
FIG. 7f is a detailed circuit schematic of the preferred embodiment of the electric circuitry of the demodulator of FIG. 7.
Figure 7G:
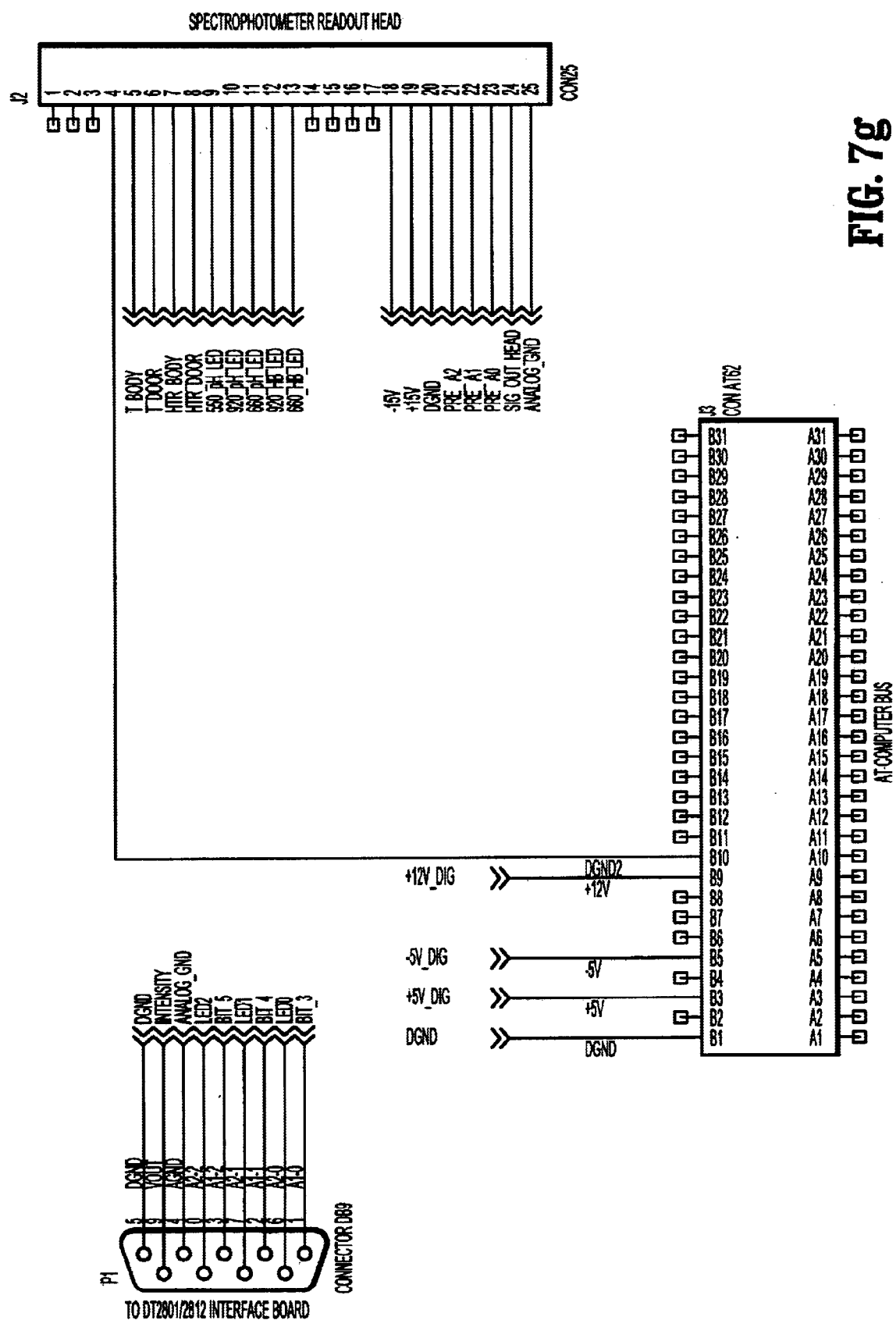
FIG. 7g is a detailed circuit schematic of the preferred embodiment of the electric circuitry of the interconnections between the major components of FIG. 7.

As shown on FIG. 7f, the resulting voltage from the multiplexer in turn is fed to second amplifier U16 to further boost the voltage amplitude of the received signal. The output of the second amplifier is fed to synchronous phase detector U17. LED clocking signals from LED drive clock generator isolator ISO1 on FIG. 7b synchronize the phase detector. The function of the phase detector is to cancel the effects of background optical noise such as extraneous light.

The output of the phase detector is fed to a third amplifier U18 configured as a low-pass filter. The third amplifier and low-pass filter boosts the light intensity voltage signal to a level sufficient for analog-to-digital conversion (for example, 0–10 volts DC) with sufficient precision (for example, 12 bits corresponding to 1 part in 4096). The low pass filter U18 provides additional attenuation of background light effects still remaining in the signal, as well as attenuation of signal modulation owing to motion and statistical signal fluctuations. A suitable cutoff frequency for such low-pass filters has been determined to be about 0.5 to 1 Hz.

The boosted and filtered light signal voltage is next applied to the analog to digital interface board for digitization. In the preferred embodiment, a Data Translation Model DT2801 board is employed. Of course, other methods of digitization well known to those of ordinary skill in the art, as well as readily available analog-to-digital integrated circuits may be employed to accomplish the required digitization.

Referring to FIG. 7b, clock circuit U6A and U7 generate the 100 Hertz clock signal which is used to drive the LEDs at the 100 Hertz frequency, and to provide the synchronous detection circuit, U17 with the appropriate detection frequency. The output of the clock circuit is fed to multiplexer circuit US which selects the appropriate LED for illumination. Address lines LED0, LED1, and LED2 are supplied by the microprocessor to select one of the 5 LEDs for illumination and measurement purposes. The selected LED clock signal is fed to one of amplifiers Us, U9, U10, U11, or U12 shown on FIG. 7c to provide the current for illuminating the LED at the 100 Hz frequency. The illumination intensity is adjusted in the preferred embodiment by variable resistors in series with each LED to achieve an appropriate measurement intensity. In the preferred embodiment this reference level was established at 1 to 5 volts at the output of the low-pass filter stage U18.

Referring to FIG. 7e, the temperature regulation circuitry is shown. Temperature sensing diodes, D2 and D3 are mounted in the readout head body and door respectively. These sensors produce a voltage proportional to the temperature sensed by the diodes. U14 and U15, preferably National Semiconductor type LM311, are configured as comparators, each with a calibrated input reference voltage and a temperature indicating voltage as a input. If the temperature input voltage is less than the reference voltage, the output voltage of the comparator will be maintained "ON" at the supply voltage of 12 volts. This voltage ensures that transistors Q2 and Q1 (or Q4 and Q3) are turned on, supplying voltage to the body (or door) heater 38 (or 60). In the preferred embodiment, the heating element is either a flexible circuit heater, or an embedded resistive element of 47 ohms value. When the voltage from the temperature sensing diode is greater than the reference voltage, the comparator is off, and the resistive heating element is de-energized. The input reference voltage in the preferred embodiment is adjusted to maintain 37 Celsius in both the body and the door of the readout head.

The DATA TRANSLATION computer interface provides selection of operational mode and acquisition of numerical results for the measurement process. Interface lines DIO-0, -1, and -2 select the infrared, red, and green LED's using a binary de-multiplexer code. DIO-3, -4, and -5 select preamplifiers U1A, U1B, and USA using a binary demultiplexer controlled by the microprocessor program. Interface line AD-0 provides input of the analog voltage to an analog-to-digital converter. One of skill in the art would readily understand how to modify the foregoing circuit to add additional or delete excess LED and photodiode pairs and appropriately adjust computer switching to obtain the desired signals.

While many means of accomplishing the required measurement process can be derived, the preferred embodiment utilizes the described circuitry and a personal computer interface, type Data Translation DT-2801. The control and computation was performed using a personal computer type Compaq Portable and software written under the ASYST laboratory computer language.

The system may be designed so that the operator initiates the pH, pCO$_2$, hemoglobin and hemoglobin oxygen saturation analysis by use of controls on the instrument, or these may be continuously and automatically accomplished by microprocessor control. In the latter instance, as the user inserts a cuvette into the instrument, photodiode output levels indicative of the presence of blood result in the microprocessor initiating the analysis.

THEORY OF OPERATION

Figure 8:
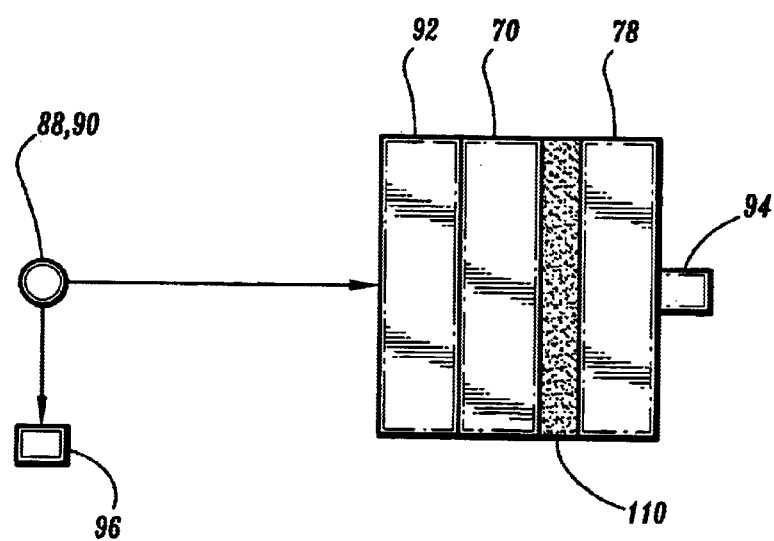
FIG. 8 is an operational diagram of the hemoglobin/hemoglobin oxygen saturation diffuse transmittance spectrophotometer.

Referring to FIG. 8, a simplified form of the invention is depicted. To perform the hemoglobin and hemoglobin oxygen saturation analysis, light is provided by a light sources 88 and 90 (however, for purposes of simplicity in reference to FIG. 8 only one light source is shown) of wavelengths selected for optimum sensitivity to hemoglobin and oxyhemoglobin, preferably either 920 nanometers and/or 660 nanometers in mean wavelength. In the preferred embodiment, this light source consists of LEDs 88 and 90, but may also be provided by laser diodes or by incandescent sources with suitable optical filters. The light from such light source 88 or 90 is diffused into an approximation of a planar random emission angle source by diffuser 92, preferably fabricated from white Teflon® or clear polymer in which titanium dioxide particles have been dispersed. This diffuse illumination is maintained by cuvette walls of cuvette halves 70 and 78, preferably fabricated from a clear polymer mixed with titanium dioxide particles. The diffuse light illuminates a blood sample 110, and is absorbed and scattered by the hemoglobin bearing erythrocytes in the whole blood sample. The scattering effects of the whole blood are minimized by the expedient of trans-illumination with diffuse light. The absorption of light by the blood sample is determined by the ratio of light intensity detected by transmittance intensity detector 94 and reference intensity detector 96, preferably large area photodiodes as shown in FIGS. 2 and 6.

The hemoglobin oxygen saturation and the hemoglobin concentration are then determined by computing the iterative solution of the following equations:

$$Hb = A + B\, T_{IR} + C\, T_{IR} \quad (1)$$

where:

Hb=hemoglobin concentration in grams/deciliter;
A=−1.324;
B=8.305;
C=2.014; and
$T_{IR}$=Io/I is the natural logarithm of the ratio of the saline reference intensity to the blood intensity for one of the LEDs (940 nm) corrected for saturation, (Ln (corrected)=−(uncorrected)+0.0035(100-Sat).

$$Sat = D(E - R) \quad (2)$$

where:

Sat=hemoglobin oxygen saturation
D=53.85 Hb/13.5; and
E=1.4+1.3×13.5/Hb
for values of Sat from 0–70%.

$$Sat = F + GR + R^2 \quad (3)$$

where:

R=[Io$_1$/I$_1$]/[Io$_2$/I$_2$]
F−108.16;
G=−7.81;
H=−14.7; and
I$_1$/I$_1$ is the saline/blood intensity ratio at one wavelength (660 nm) and Io$_2$/I$_2$ is the saline/blood intensity ratio at a second wavelength (940 nm), for values of Sat from 70–100%.

Solution of these equations may be obtained in a number of ways, but in accordance with the preferred embodiment, the solution is achieved by a programmed computer using an iterative method based upon an initial calibration of saturation using equation (3).

Figure 9:
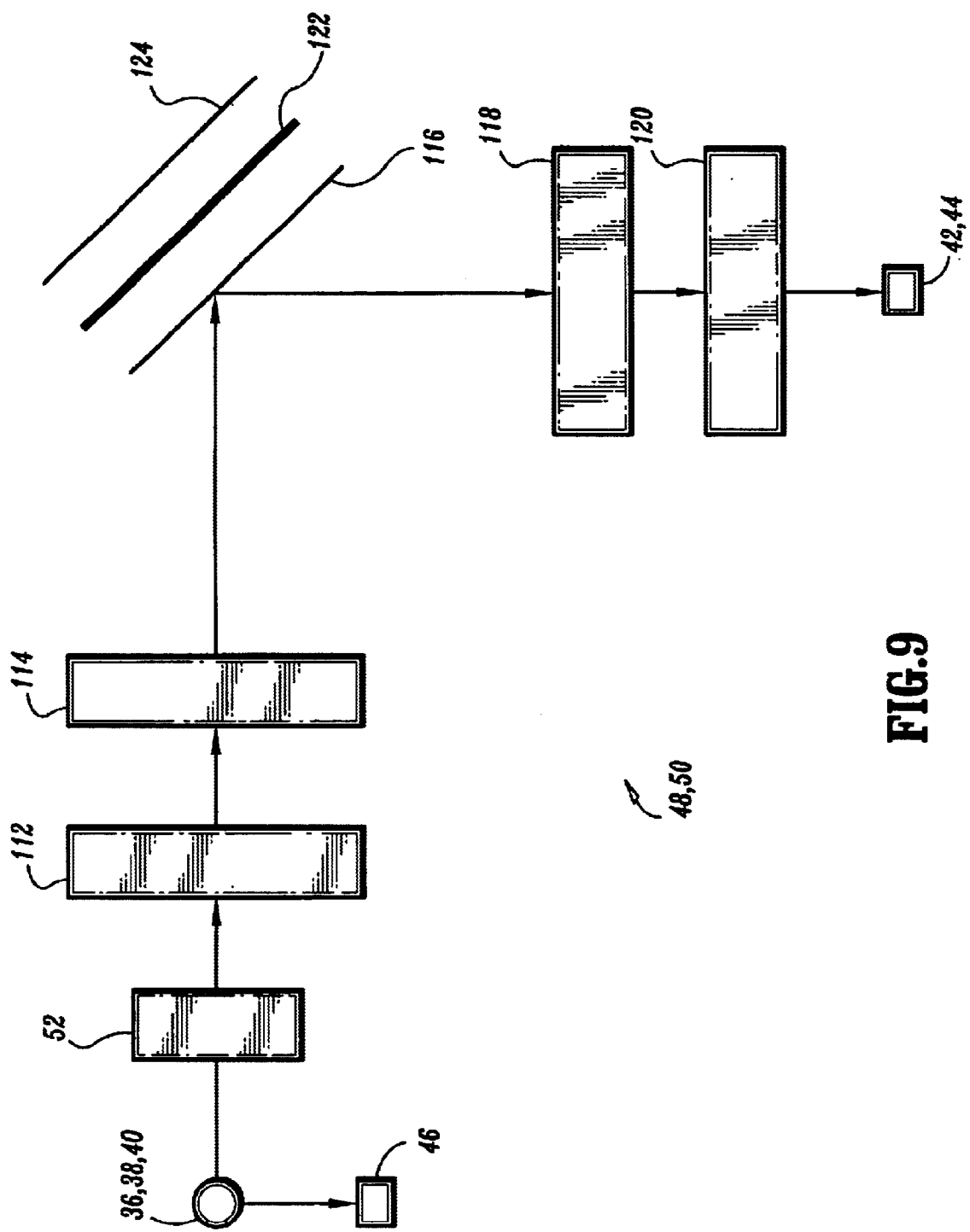
FIG. 9 is an operational diagram of the pH/pCO$_2$ reflectance spectrophotometer.

Referring now to FIG. 9, wherein a simplified view of the dual channel transmission/reflectance system for pH and pCO$_2$ measurement is shown utilizing only one light source which typifies all three light sources 36, 38, and 40 of FIGS. 2 and 6. Furthermore, only one photodiode 42, 44, and 46 is shown on conjunction with diffuser 52. This is done to simplify the theory of operation for both the pH and pCO$_2$ measurement, while only, in fact, discussing the operation of one such measurement. The operation of both systems is the same. While the wavelengths of the light sources can be determined by optical filtering of broadband visible light sources, in the preferred embodiment, the sources are comprised of laser diodes or light emitting diodes that are selected for the appropriate emission spectra. The light sources are aligned in a unique arrangement that provides relatively equal illumination to two separate illumination paths for sensing of pH and pCO$_2$, and which provides further illumination to a reference intensity sensor. In the preferred embodiment, the arrangement of the optical devices is such that illumination provides for transmission absorption spectrophotometric determination of the ratio of hydrogen ion bound dye to dye which is not hydrogen ion bound.

Light of wavelength $\lambda_1$ is transmitted from light sources 36, 38, and/or 40 through diffuser 52, sensors 48 and/or 50. Sensors 48 and 50 include a substrate 112, through hydrogel dye laden layer 114 to reflective layer 116, back through dye laden layer 118 and substrate 120 to detecting photodiode 42 and 44. Opaque absorber 122 effectively shutters out stray light, which might reach the body fluid and be reflected back to the detecting photodiode. Reference photodiode 46 monitors the source light intensity for any variations. Hydrophobic gas permeable membrane 124 permits diffusion of water vapor and CO$_2$ from the fluid under measurement to the hydrogel layer for detection.

Light intensity at the detecting photodiode ($I_d$) as a function of the light emitted from the source(s) ($I_s$) is given by:

$$I_d = I_s \exp[-f(l_1, \lambda_1)] \exp[-g(pH, l_2, C_D, \lambda_1)] \exp[-h(C_R, \lambda_1)]$$

$$\exp[-f(l_1, \lambda_1)] \times \exp[-g(pH, l_2, C_D, \lambda_1)]$$

where:

$l_1$ is the length of the substrate through which the light passes on it way to the detector.
$\lambda_1$ is the wavelength of one of the light sources.
$l_2$ is the length of the pH sensitive hydrogel layer.
$C_D$ is the concentration of the pH sensitive dye.
$C_R$ is the concentration of the reflective pigment.

A similar equation can be written for each additional wavelength of light that is utilized. ($\lambda_2, \lambda_3$, etc.)

Since $I_{Ref}$ is simply a constant times $I_s$, the natural logarithm of $I_s/I_{Ref}$ is given by:

$$K_1 - [2f(l_1, \lambda_1)] - [2g(pH, l_2, C_D, \lambda_1)] - [h(C_R, \lambda_1)]$$

For a suitable sensor readout head, the only significant variables are the wavelengths and the pH. Since the wavelengths are pre-determined, there will be a 1:1 correspondence between the pH of the dye layer hydrogel and the light transmission ratios of the dye layer to differing wavelengths of light. The device currently described provides such suitable performance.

An improvement of the present device is the incorporation of two separate spectrophotometric channels and sensors for the simultaneous determination of pH and pCO$_2$ with a cuvette capable of having optically diffuse walls with a separate chamber for diffuse transmittance determination of hemoglobin and hemoglobin oxygen saturation, all from the same body fluid sample. A unique optical geometry allows both the pH and pCO$_2$ sensors to be illuminated by the same optical sources(s) in a combination of transmission sensing of the dye concentrations(s) and reflection return of light to the measurement sensors that eliminates optical cross coupling of the measurements, and which eliminates optical effects of the body fluid which might otherwise interfere with the measurement process. This feature is incorporated in the device by means of addition of an optical diffuser at the intersection of the optical source paths and the illumination paths for each of the two sensing elements. The diffuser helps provide for equal illumination of the two sensing elements. The illumination paths of the two sensing elements intersect at a 90-degree angle with the source path, and additionally intersect with the sensing elements at an angle, which is 45 degrees above the horizontal. The measurement intensity sensing optical path intersects with the sensor surface at a oblique angle to that of the source optical path, 135 degrees to the direction of illumination and 45 degrees to the surface. The source and sensing optical paths cross only within the clear housing of the sensor element, further reducing the possibility of direct transmission of light from the source to the intensity-sensing detector.

It is a further improvement of the device that the entirety of the optical sensing element is maintained at 37 degrees Celsius. This feature provides for pH and $pCO_2$ determination at normal human body temperature, eliminating the correction of the measurement to normal standard levels.

By utilizing a spectrophotometric means employing discrete wavelengths of electromagnetic radiation directed through a cuvette containing a sample of whole, nonhemolyzed blood, the present invention provides a compact, bedside apparatus for real time measurement of blood hemoglobin oxygen saturation and hemoglobin concentration, and for determination of blood pH and $pCO_2$. In the preferred embodiment, the cuvette is removable from the sensing unit and thus provides an inexpensive disposable item.

OPERATION OF THE MEASURING DEVICE

In normal operation, the device is connected to a power source such that the readout head 24 is heated to its normal operation temperature of 37 degrees Celsius. The sensing cuvette 26 comprised of a fluid path and two photodiodes for sensing of pH and $pCO_2$ are installed in the device, awaiting introduction of a body fluid, such as blood for analysis. A separate optical channel, which trans-illuminates the fluid path continuously, monitors the cuvette for the presence of a body fluid for analysis. Upon introduction of a sample into the cuvette, as detected by a reduction in the light transmitted through the cuvette, a timing process begins which allows the pH and $pCO_2$ sensor to hydrate and to come into chemical equilibrium with the fluid under analysis. After a pre-determined time, typically two to three minutes, the light sources are sequentially enabled and the light intensity reflected from the pH and $pCO_2$ sensors at each of the measurement wavelengths is measured. The reflected light intensity is compared with calibration data which has been obtained from both fully reflective (white) and fully absorptive (black) calibration sensor devices, and an equivalent optical transmittance is calculated at each wavelength. The optical transmittance is compared with calibration data which has been stored in computer memory, which is indicative of the pH and $pCO_2$ for the sensors in the cuvette, and the resultant calculated pH and $pCO_2$ values are displayed. In the preferred embodiment, the calculation is performed from quadratic curve-fit data obtained for the specific pH sensitive dye, reflector layer and absorber layer for the described type of optode. A computer program capable of automatically sensing the introduction of body fluid such as whole blood into the measurement cuvette, automatically determining the optical transmittance of various wavelengths of light by the pH and $pCO_2$ sensors, and calculating and displaying the resultant pH and $pCO_2$ is provided in Appendix A.

The pH and $pCO_2$ measurement is accomplished by sequentially turning on each of the LEDs in the reflectance spectrophotometer, and measuring the resultant voltage in both the reflectance photodiodes and in the reference photodiode. The computing device manipulates the ratios of the resulting intensities as follows:

$$RpHI_{IR} = IpH_{920}/Io_{920} \quad (4)$$

$$RpHI_R = K_1 \times IpH_{660}/Io_{660} \quad (5)$$

$$RPHI_G = K_2 \times IpH_{550}/Io_{550} \quad (6)$$

$$R_{pH} = RpHI_R/RpHI_G \quad (7)$$

$$pH = A_{pH0} + [A_{pH1} \times R_{pH}] + [A_{pH2} \times R_{pH2}] \quad (8)$$

where:

$IpH_{920}$=voltage proportional to the intensity of light reflected from the pH sensor with the infrared LED energized.

$Io_{920}$=voltage proportional to the intensity of light at the reference photodiode with the infrared LED energized.

$IpH_{660}$=voltage proportional to the intensity of light reflected from the pH sensor with the red LED energized.

$Io_{660}$=voltage proportional to the intensity of light at the reference photodiode with the red LED energized.

$IpH_{550}$=voltage proportional to the intensity of light reflected from the pH sensor with the green LED energized.

$Io_{550}$=voltage proportional to the intensity of light at the reference photodiode with the green LED energized.

K1 and K2 are constants utilized to correct the measured values at each of specific wavelengths to factors measured at initial factory calibration.

$A_{pH0}, A_{pH1}$, and $A_{pH2}$, are polynomial factors to which the pH data from a representative set of sensors has been fit by linear regression techniques. These factors are stored in the computing device and are specific for a particular batch of sensors.

Similarly, for the determination of $PCO_2$:

$$RpCI_{IR} = IPC_{920}/Io_{920} \quad (9)$$

$$RpCI_R = K_3 \times IpC_{660}/Io_{660} \quad (10)$$

$$RpCI_G = K_4 \times IpC_{550}/Io_{550} \quad (11)$$

$$RpC = RpCI_R/RPCI_G \quad (12)$$

$$PCO_2 = A_{pC0} + [A_{pC1} \times R_{pC}] + [A_{pC2} \times R_{pC2}] \quad (13)$$

where:

$IpC_{920}$=voltage proportional to the intensity of light reflected from the $pCO_2$ sensor with the infrared LED energized.

$Io_{920}$=voltage proportional to the intensity of light at the reference photodiode with the infrared LED energized.

$IpC_{660}$=voltage proportional to the intensity of light reflected from the $PCO_2$ sensor with the red LED energized.

$Io_{660}$=voltage proportional to the intensity of light at the reference photodiode with the red LED energized.

$IpC_{550}$=voltage proportional to the intensity of light reflected from the $pCO_2$ sensor with the green LED energized.

$Io_{550}$=voltage proportional to the intensity of light at the reference photodiode with the green LED energized.

K3 and K4 are constants utilized to correct the measured values at each of specific wavelengths to factors measured at initial factory calibration.

$A_{pC0}, A_{pC1}$, and $A_{pC2}$, are polynomial factors to which the $pCO_2$ data from a representative set of sensors has been fit by linear regression techniques. These factors are stored in the computing device and are specific for a particular batch of sensors.

By utilizing a novel reflective spectrophotometric means employing discrete wavelengths of electromagnetic radiation directed through a cuvette containing a sample of whole blood, the present invention provides a compact, bedside apparatus for real time measurement of blood pH and $pCO_2$.

The combination of the novel reflective spectrophotometer with a novel diffuse transmissive spectrophotometer permits the simultaneous determination of pH, $pCO_2$, hemoglobin, and hemoglobin oxygen saturation.

In the preferred embodiment, the cuvette is removable from the sensing unit and thus provides an inexpensive disposable item.

Sufficient detail has been included in the foregoing description of the circuitry of a preferred embodiment of an electronic instrument for use with the invention.

Having described the invention with particular reference to the preferred form thereof, it will be apparent to those skilled in the art to which the invention pertains after understanding the invention, that various changes and modifications may be made therein without departing from the scope of the invention as defined by the claims appended hereto.

What is claimed is:

1. Apparatus for use in measuring molecular constituents of a sample of light dispersive fluids comprising:
   a housing having an optically transmissive chamber for receiving a sample of light dispersive fluid;
   first and second light sources respectively having first and second narrow bands of wavelengths, said first and second light sources being oriented to illuminate a sample in the chamber when the light sources are transmitting light;
   a first and second sensors adapted to respectively detect the first and second narrow bands of wavelengths; and
   a diffuser including an optically transmissive material containing a dispersion of non-absorptive light-scattering particles disposed between the sample and at least one of the light sources, and adapted to diffuse the light from said at least one of said light sources incident on the sample; said first and second narrow bands of wavelengths and said first and second sensors being respectively selected to detect pH and pCO2 of such sample.

2. Apparatus for use in measuring molecular constituents of a sample of whole blood comprising:
   a housing having an optically transmissive chamber for receiving a sample of light dispersive fluid;
   first and second light sources respectively having first and second narrow bands of wavelengths, said first and second light sources being oriented to illuminate a sample in the chamber when the light sources are transmitting light;
   first and second sensors adapted to respectively detect the first and second narrow bands of wavelengths; and
   a diffuser including an optically transmissive material containing a dispersion of non-absorptive light-scattering particles disposed between the sample and at least one of the light sources and adapted to diffuse the light from said at least one of said light sources incident on the sample; the first and second narrow bands of wavelengths and said first and second sensors being respectively selected for the determination of hemoglobin concentration and/or hemoglobin oxygen saturation in said sample.

3. Apparatus for use in measuring molecular constituents of a sample of whole blood comprising:
   a housing having an optically transmissive chamber for receiving a sample of light dispersive fluid;
   first and second light sources respectively having first and second narrow bands of wavelengths, said first and second light sources being oriented to illuminate a sample in the chamber when the light sources are transmitting light;
   first and second sensors adapted to respectively detect the first and second narrow bands of wavelengths; and
   a diffuser including an optically transmissive material containing a dispersion of non-absorptive light-scattering particles disposed between the sample and at least one of the light sources and adapted to diffuse the light from said at least one of said light sources incident on the sample; the first and second narrow band wavelengths and said first and second sensors being respectively selected for the determination of one or more of the molecular constituents selected from the group consisting of oxyselected hemoglobin, deoxygenated hemoglobin, carboxyhemoglobin, methemoglobin, or hemoglobincyanide of said sample.

4. An indicator arrangement comprising at least two narrow band light sources, optical diffusers, diffusing cuvette and light detector for determination of molecular constituents of light dispersing fluids, the improvement comprising providing an indication that is insensitive to the light scattering effects of suspended particles.

5. An indicator arrangement as defined in claim 4 wherein said measurement system is effected by means of a light measurement system including a light source, diffuse optical system, a light receiver and readout means.

6. An indicator arrangement as defined in claim 4 wherein said measurement is effected by means of one or more light emitting diodes selected for determination of the hemoglobin concentration in whole blood.

7. An indicator arrangement as defined in claim 4 wherein said measurement is effected by one or more optional filters selected for determination of the hemoglobin concentration in whole blood.

8. An indicator arrangement as defined in claim 4 wherein said measurement is effected by two or more light sources whose wavelengths are selected for determination of oxy-selected hemoglobin, dioxygenated hemoglobin, carboxyhemoglobin, methemoglobin, or hemiglobincyanide.

9. An indicator arrangement as defined in claim 4 further comprising a disposable cuvette.

10. An apparatus for use in providing in-vivo, real time measurement of blood pH, pCO2, hemoglobin, and hemoglobin oxygen saturation, comprising:
    a disposable cuvette having an optically transmissive housing containing first, second, and third blood chambers and first and second sensors for measurement of pH, pCO2, hemoglobin, and hemoglobin oxygen saturation;
    first and second light sources respectively having first and second narrow band of wavelengths, said first and second light sources being oriented to illuminate the first and second sensors for sensing of pH and pCO2 in the first and second blood chambers, respectively; and third and fourth light sources respectively having third and fourth narrow band of wavelengths, respectively, said third and fourth light sources being oriented to illuminate a blood sample in the third blood chamber when the third and fourth light sources are transmitting light;

means for detecting the first, second, third, and fourth narrow band of wavelengths from each of the first, second, third, and fourth light sources; and diffuser means for providing the light illuminating the first, second, and third blood chambers with a broad angular dispersion so that the light incident on the blood samples approaches a diffuse planar source of light, the diffuser means being disposed between the light sources and the blood sample.

11. The apparatus of claim 10 wherein the diffuser means further comprises an optically transmissive material containing a dispersion of non-absorption light-scattering particles.

12. An apparatus for use in providing in-vivo, real time measurement of selected blood characteristics, comprising:

a housing containing at least one optically transmissive blood chamber for receiving a sample of blood;

at least two light sources, each providing illumination within a narrow band of wavelengths, each of said light sources being oriented to illuminate first and second sensor assemblies for detecting pH and pCO2 of a blood sample in said blood chamber when the light sources are transmitting light, wherein the first and second sensor assemblies include pH and pCO2 sensitive hydrogel layers, reflective layers, opaque layers, and appropriate blood contact layers.

13. An apparatus for use in providing in-vivo, real time measurement of blood pH, pCO2, hemoglobin, and hemoglobin oxygen saturation, comprising:

a general purpose computing device for displaying various measured values, user controls and for storing the operating instructions for the apparatus;

a first interface card containing the electronic control and signal conditioning circuitry;

a second interface card for providing connection of the computing device to analog signals and digital signals for controlling the apparatus;

a spectrophotometer providing specific wavelength visible and infra-red light sources and light intensity detection sensors;

a cuvette for introduction of blood for analysis containing the pH and pCO2 sensors; and connective inlet and outlet tubing for introduction of the blood sample from invasive patient monitoring lines into the cuvette and for return of the blood sample to the patient a diffuser disposed between the sample and at least one of the light sources adapted to diffuse the light from at least one of said light sources with a broad angular dispersion so that the light incident on the sample approaches a diffuse planar source of light.

14. Apparatus for use in measuring molecular constituents of a sample of whole blood comprising:

a housing having an optically transmissive chamber for receiving a sample of whole blood;

first and second light sources respectively having first and second narrow bands of wavelengths, said first and second light sources being oriented to illuminate a sample in the chamber when the light sources are transmitting light;

a sensor adapted to detect the first and second narrow band of wavelengths; and a diffuser disposed between the sample and at least one of the light sources, said diffuser adapted to diffuse the light from at least one of said light sources incident on the sample, wherein said diffuser is further adapted to diffuse the light from said at least one light source with a broad angular dispersion so that the light incident on the sample approaches a diffuse planar source of light, the first and second narrow bands of wavelengths being selected for the determination of hemoglobin concentration and/or hemoglobin oxygen saturation in whole blood, a heater assembly for maintaining the blood in the sample chamber at a desired temperature.

15. Apparatus for use in measuring molecular constituents of a sample of whole blood comprising:

a housing having an optically transmissive chamber for receiving a sample of whole blood;

first and second light sources respectively having first and second narrow bands of wavelengths, said first and second light sources being oriented to illuminate a sample in the chamber when the light sources are transmitting light;

a sensor adapted to detect the first and second narrow band of wavelengths; and a diffuser disposed between the sample and at least one of the light sources, said diffuser adapted to diffuse the light from at least one of said light sources incident on the sample, wherein said diffuser is further adapted to diffuse the light from said at least one light source with a broad angular dispersion so that the light incident on the sample approaches a diffuse planar source of light, the first and second narrow bands of wavelengths are selected for the determination of one or more of the molecular constituents selected from the group consisting of oxyselected hemoglobin, dioxygenated hemoglobin, carboxyhemoglobin, methemoglobin, or hemiglobincyanide, a heater assembly adapted to maintain the sample at a desired temperature.

16. An apparatus for use in providing in-vivo, real time measurement of selected blood characteristics, comprising:

a housing containing at least one optically transmissive blood chamber for receiving a sample of blood;

at least two light sources, each providing illumination within a narrow band of wavelengths, each of said light sources being oriented to illuminate first and second sensor assemblies for detecting pH and pCO2 of a blood sample in said blood chamber when the light sources are transmitting light, the housing including first and second optically transmissive blood chambers for receiving a sample of blood;

the first light source being oriented to illuminate the first sensor for detecting pH of a blood sample in the first blood chamber;

the second light source being oriented to illuminate the second sensor for detecting pCO2
of a blood sample in the second blood chamber.

17. The apparatus of claim 16 wherein the first and second sensors are photodiodes for sensing the pH and pCO2 of the blood sample found within the first and second blood chambers.

18. An apparatus for use in providing in-vivo, real time measurement of selected blood characteristics, comprising:
- a housing containing at least one optically transmissive blood chamber for receiving a sample of blood;
- at least two light sources, each providing illumination within a narrow band of wavelengths, each of said light sources being oriented to illuminate first and second sensor assemblies for detecting pH and pCO2 of a blood sample in said blood chamber when the light sources are transmitting light,
- means for maintaining the blood in the blood chambers at a desired temperature.

19. The apparatus of claim 18 wherein the first and second sensor assemblies for detecting the pH and pCO2 of the blood sample include first and second light sensing elements and first and second reflective assemblies of pH and pCO2, respectively, sensitive dye layers.

20. An apparatus for use in providing in-vivo, real time measurement of selected blood characteristics, comprising:
- a housing containing at least one optically transmissive blood chamber for receiving a sample of blood;
- at least two light sources, each providing illumination within a narrow band of wavelengths, each of said light sources being oriented to illuminate first and second sensor assemblies for detecting pH and pCO2 of a blood sample in said blood chamber when the light sources are transmitting light,
- the first and second sensor assemblies for detecting the pH and pCO2 of the blood sample include first and second light sensing elements and first and second reflective assemblies of pH and pCO2, respectively, sensitive dye layers,
- the first and second reflective elements of the first and second sensor assemblies being oriented with each light source and with the first and second light sensing elements to be illuminated by each light source through the blood sample and to illuminate the respective first and second light sensing elements;
- the housing including an optical diffuser at the intersection of the light paths between the light sources, the reflective elements and the light sensing elements to provide for equal illumination of the light sensing elements; and
- the light sources being sequentially stroked to provide illumination at each narrow band of wavelengths on the first and second sensor assemblies sensor at different times.

21. The apparatus of claim 20 wherein the pH and pCO2 sensitive indicators comprise assemblies of pH and pCO2, respectively, sensitive hydrogel layers, reflective layers, opaque layers, and appropriate blood contact layers.

22. The apparatus of claim 21 wherein
- the first and second reflective elements of the first and second sensor assemblies are oriented with each light source and with the first and second light sensing elements to be illuminated by each light source through the blood sample and to illuminate the respective first and second light sensing elements;
- the housing includes an optical diffuser at the intersection of the light paths between the light sources, the reflective elements and the light sensing elements to provide for equal illumination of the light sensing elements.

23. An apparatus for use in providing in-vivo, real time measurement of selected blood characteristics, comprising:
- a housing containing at least one optically transmissive blood chamber for receiving a sample of blood;
- at least two light sources, each providing illumination within a narrow band of wavelengths, each of said light sources being oriented to illuminate first and second sensor assemblies for detecting pH and pCO2 of a blood sample in said blood chamber when the light sources are transmitting light,
- the housing including an additional optically transmissive blood chamber for receiving a sample of blood;
- third and fourth light sources respectively having third and fourth narrow bands of wavelengths, said third and fourth light sources being oriented to illuminate a blood sample in the additional blood chamber when the third and fourth light sources are transmitting light;
- a sensor adapted to detect the third and fourth narrow bands of wavelengths; and
- a diffuser disposed between the sample and the third and fourth light sources, said diffuser adapted to diffuse the light from the third and fourth light sources incident on the sample.

24. The apparatus of claim 23 wherein the third and fourth narrow band wavelengths are selected for the determination of one or more of the molecular constituents selected from the group consisting of oxyselected hemoglobin, deoxygenated hemoglobin, carboxyhemoglobin, methemoglobin, or hemoglobincyanide.

25. The apparatus of claim 23 wherein the first and second sensors comprise photodiodes.

26. The apparatus of claim 23 wherein the third and fourth sensors comprise transmission intensity detectors.

27. The apparatus of claim 26 wherein the detectors are large area photodiodes.

28. The apparatus of claim 23 wherein the third and fourth narrow bands of wavelengths are selected for the determination of hemoglobin concentration and/or hemoglobin oxygen saturation in whole blood.

29. The apparatus of claim 23 wherein said diffuser is further adapted to diffuse the light from said third and fourth light sources illuminating the sample in the additional blood chamber with a broad angular dispersion so that the light incident on the sample in said additional blood chamber approaches a diffuse planar source of light.

30. The apparatus of claim 23 wherein the diffuser further comprises an optically transmissive material containing a dispersion of non-absorption light-scattering particles.

31. The apparatus of claim 23 wherein the apparatus includes means for maintaining the blood in the blood chambers at a desired temperature.

32. A method for determining the pH and/or pCO2 of a sample of blood comprising:
- drawing a sample of blood into a housing having at least one optically transmissive chamber for receiving the sample;
- contacting the sample with pH and pCO2 sensitive reflective indicators;
- illuminating the indicators with light from at least two light sources each having a narrow band of wavelengths;
- determining the reference intensity of the light from each light source incident on the indicators;
- reflecting each narrow band of wavelengths from each indicator to at least one light sensor;
- sensing the reflected light with the light sensor; and
- determining the pH and/or pCO2 of the sample based on the relative amounts of light reflected by pH and pCO2 reflective indicators and the reference intensity.

33. The method of claim 32 wherein the illuminating step further comprises:

sequentially stroking the light sources at different times to illuminate the reflective indicators and the light sensor with each narrow band of wavelengths at a different time.

34. The method of claim 32 further comprising the steps of:

drawing the blood sample into at least one additional optically transmissive chamber of the housing;

illuminating the sample from at least two additional light sources with light having narrow bands of wavelengths appropriate for the determination of hemoglobin concentration and/or hemoglobin oxygen saturation in the blood sample in the additional chamber;

determining the reference intensity of the light from the additional light sources incident on the sample in the additional chamber;

diffusing the light from the additional light sources incident on the sample in the additional chamber;

detecting the diffused light from the additional light sources transmitted through the sample in the additional chamber; and determining the hemoglobin concentration and/or hemoglobin oxygen saturation of the sample based on the relative amounts of light from the additional light sources absorbed by the sample in the additional chamber.

35. The method of claim 34 wherein the illuminating and determining steps further comprise:

illuminating the sample in the additional chamber from the additional light sources with light having narrow bands of wavelengths appropriate for the determination of one or more of the molecular constituents selected from the group consisting of oxyselected hemoglobin, deoxygenated hemoglobin, carboxyhemoglobin, methemoglobin, or hemoglobincyanide; and determining one or more of the molecular constituents of the blood sample based on the relative amounts of light from the additional light sources absorbed by the sample in the additional chamber, the molecular constituents selected from the group consisting of oxyselected hemoglobin, deoxygenated hemoglobin, carboxyhemoglobin, methemoglobin, or hemoglobincyanide.

36. The method of claim 34 wherein said diffusing step further comprises:

diffusing the light from each light source illuminating the sample with a broad angular dispersion so that the light incident on the sample approaches a diffuse planar source of light.

37. The method of claim 34 wherein said diffusing step further comprises:

passing the light through an optically transmissive material containing a dispersion of non-absorptive light-scattering particles.

38. The method of claim 34 wherein said diffusing step further comprises:

passing the light through an optically transmissive material containing a dispersion of non-absorptive light-scattering particles; and diffusing the light from each light source illuminating the sample with a broad angular dispersion so that the light incident on the sample approaches a diffuse planar source of light.

* * * * *